(12) United States Patent
D'Andrea

(10) Patent No.: US 7,459,287 B2
(45) Date of Patent: Dec. 2, 2008

(54) METHOD FOR DETERMINATION AND QUANTIFICATION OF RADIATION OR GENOTOXIN EXPOSURE

(75) Inventor: Alan D. D'Andrea, Winchester, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 254 days.

(21) Appl. No.: 11/046,346

(22) Filed: Jan. 28, 2005

(65) Prior Publication Data
US 2005/0255502 A1    Nov. 17, 2005

Related U.S. Application Data

(60) Provisional application No. 60/540,380, filed on Jan. 30, 2004.

(51) Int. Cl.
*G01N 33/533*    (2006.01)
(52) U.S. Cl. ..................... 435/40.51; 435/29
(58) Field of Classification Search ............. None
See application file for complete search history.

(56) References Cited

U.S. PATENT DOCUMENTS

| 5,371,004 A | 12/1994 | Quintern |
| 6,025,336 A | 2/2000 | Goltry et al. |
| 6,090,539 A | 7/2000 | Haaf et al. |
| 6,362,317 B1 | 3/2002 | Bonner et al. |
| 2003/0093819 A1 | 5/2003 | D'Andrea et al. |
| 2003/0143533 A1 | 7/2003 | Haaf et al. |

FOREIGN PATENT DOCUMENTS

WO    WO 01/91629 A2    12/2001

OTHER PUBLICATIONS

None cited.*
Tanaguchi, T. et al. The Franconia anemia protein, FANCE, promotes the nuclear accumulation of FANCC. Blod. Oct. 1, 2002, vol. 100, No. 7, pp. 2457-2462.
Tanaguchi, T. et al., S phase-specific interaction of the Fanconi anemia protein, FANCD2, with BRCA1 and RAD51. Blood. Oct. 1, 2002, vol. 100, No. 7, pp. 2414-2420.
Garcia-Higuera, I., Taniguchi, T., Ganesan, S., Meyn, M. S., Timmers, C., Hejna, J., Grompe, M., and D'Andrea, A. D. (2001). Interaction of the Fanconi anemia proteins and BRCA1 in a common pathway. Mol Cell 7, 249-262.

* cited by examiner

*Primary Examiner*—James Martinell
(74) *Attorney, Agent, or Firm*—Edwards Angell Palmer & Dodge LLP; Kathleen Williams; Matthew Beaudet

(57) ABSTRACT

The present invention discloses methods for detecting exposure of a living subject to genotoxic agents, testing sensitivity to a genotoxic agent, and determining DNA damage caused by exposure to an agent, comprising detecting the presence of FANCD2-containing foci from a sample collected from said subject. The presence of concentrated foci is indicative of DNA damage, and the degree of foci formation is correlated with degree of exposure. Diagnostic reagents contain a ligand that binds to human FANCD2 associated with a detectable label. Kits for detecting DNA damage in a biological sample contain such diagnostic reagents and signal detection components. The invention further discloses methods for identifying agents which modulate the ability of FANCD2-containing foci to form. Among other things, such agents are potentially useful chemosensitizing agents or may confer protection against damage caused by genotoxic agents.

5 Claims, 14 Drawing Sheets

Figure 2. Monoubiquitination of the GFP-FANCD2 fusion protein In stably transfected FA-D2 human fibroblasts Figure 4
Subcloning of a cell line which expresses EGFP-D2 moderately and is suitable for the assay PD20F+EGFP-FANCD2 clone 7
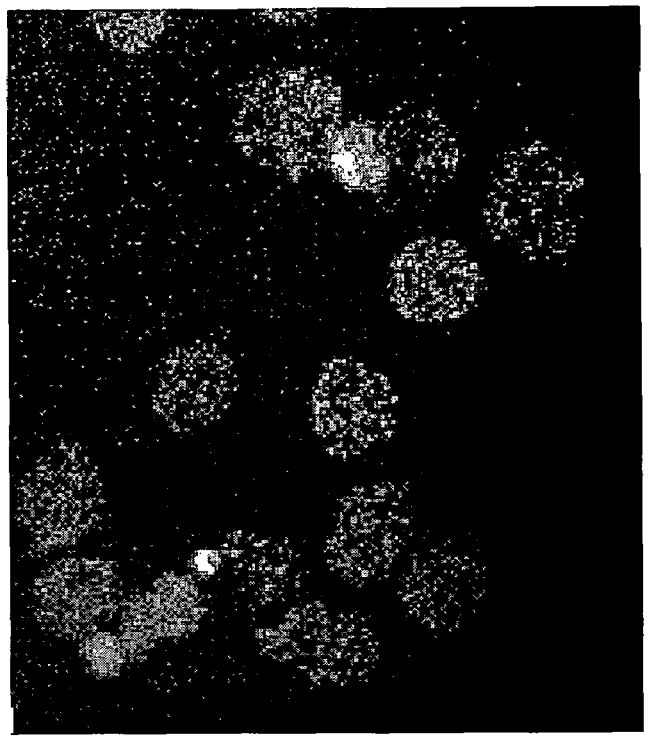
IR15Gy-12hr
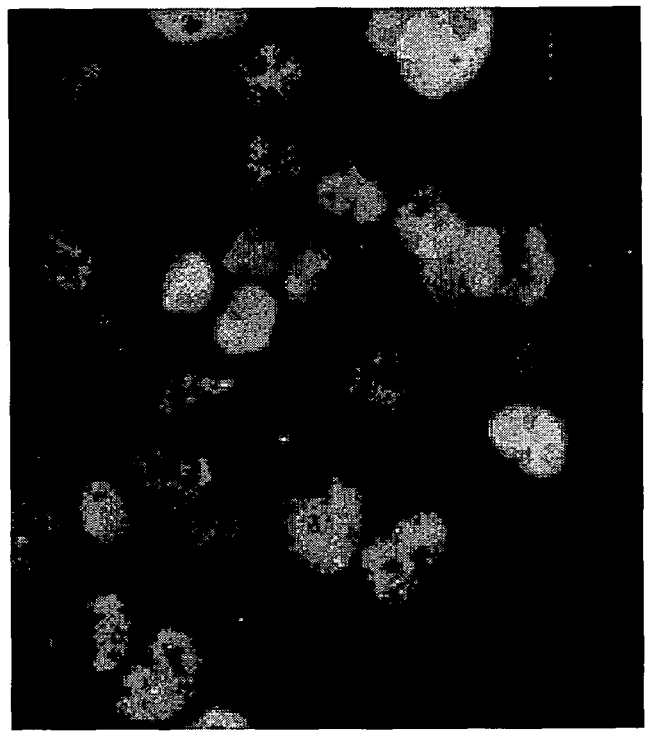
untreated
EGFP Figure 6 FA pathway inhibitors screening protocol
EGFP-FANCD2 nuclear foci assay

METHOD FOR DETERMINATION AND QUANTIFICATION OF RADIATION OR GENOTOXIN EXPOSURE

RELATED APPLICATIONS

This application is a utility application which claims priority under 37. U.S.C. § 119(e) to U.S. Provisional Application Ser. No. 60/540,380, filed Jan. 30, 2004, the entirety of which is incorporated herein by reference.

FIELD OF THE INVENTION

This invention relates to detecting exposure of a living subject to genotoxic agents, such as radiation and environmental toxins. Methods are also provided which facilitate the identification of therapeutic compounds for cancer treatment and protection against genotoxic agents.

BACKGROUND OF THE INVENTION

Chemotherapy and radiotherapy constitute common treatments for many diseases. Although such methods of therapy can be used effectively in the therapy of diseases such as cancer, exposure to biologically significant levels of radiation can also cause genotoxic stress. Similarly, many industrial processes (such as the production of nuclear power) and military uses (such as nuclear weapons) can expose individuals to hazardous levels of genotoxic agents. Such exposure can elicit a variety of cellular responses, ranging from cell-cycle arrest to mutation, malignant transformation, or cell death.

Due to individual genetic make-up, some people have defective DNA repair mechanisms, resulting in chromosome instability. There are three main consequences of such chromosome instability. These individuals may have (1) developmental abnormalities (birth defects), (2) predisposition to cancers, and (3) hypersensitivity of their tissues to radiation and chemotherapy.

In severe cases, such individuals may be born with an obvious genetic disease (i.e., Fanconi Anemia). This disease results from a complete knockout of both alleles of a particular DNA repair gene. In less severe and more common cases, individuals may have a partial disruption of a DNA repair gene or pathway. Such a disruption may result from inheriting a "variant" DNA repair gene, such as a single nucleotide polymorphism in a Fanconi Anemia (FA) gene. While these individuals may have normal development (i.e., no evidence of birth defects), the only clinical sequelae of their genetic weakness may be the early onset of cancer, or radiation or drug sensitivity. The identification of such individuals, before they develop cancer or before they develop life-threatening toxicity from radiation/drug exposure, is an important, unsolved problem in clinical medicine.

Predicting radiation/chemotherapy toxicity is difficult and relies, at present, on circumstantial evidence. First, individuals who have early onset of rare cancers or strong family histories of cancer, with clear autosomal dominant or recessive inheritance, may have an underlying genetic defect. In these cases, culprit cancer susceptibility genes (BRCA1, BRCA2, p53) can be sequenced to confirm or rule out the defect. Second, individuals who have subtle clinical findings, reminiscent of a more preformed genetic disease (i.e. skin café au lait spots or short stature), may have an underlying DNA repair disorder.

Efforts to predict which cancer patients have an underlying DNA repair disorder have been largely ineffectual. While FA patients and Blooms syndrome patients have obvious (measurable) defects in chromosome breakage, patients with more subtle DNA repair disorders do not score positive in typical chromosome breakage studies. Standard doses of radiation/chemotherapy are given to all cancer patients, depending on the specific tumor type and location. Approximately 2% of these patients may have unexpected severe toxic reactions, as the first evidence of their underlying DNA repair disorder.

There is a need in the art for a method of detecting exposure to a genotoxic agent in a live sample (i.e., a so-called biological dosimeter). There is also a need in the art for methods of testing an individual's sensitivity to a genotoxic agent. There is also a need in the art for a method of determining damage caused to an individual by exposure to a genotoxic agent. There also exists a need in the art for a method to identify agents which are active in modulating the responses of cells toward genotoxic agents. There also exists a considerable need to obtain compounds which are active in protecting an individual from probable exposure to a genotoxic agent such as radiation and genotoxic carcinogens.

SUMMARY OF THE INVENTION

The present invention discloses methods and compositions that are useful in detecting exposure of a living subject to genotoxic agents. These methods and compositions are based on the observation that FANCD2 and other proteins form nuclear foci in cells exposed to genotoxic agents. The invention also encompasses compositions and methods that are useful in identifying modulators of foci formation.

In one aspect, the invention provides for a method of detecting exposure to a genotoxic agent in a live subject, comprising the following steps: collecting a sample from the subject; and detecting the presence of FANCD2-containing foci in the sample. Presence of foci is indicative of exposure to a genotoxic agent. The subject can be human. The sample can be selected from a group consisting of peripheral blood, saliva, urine, a cell scraping, exudate, a buccal sample, sputum, and cervical scraping. In a preferred embodiment, the sample is peripheral blood. Alternatively, the method can further comprise a control sample, where the degree of foci formation in the sample relative to a control sample is indicative of the degree of exposure of the subject to a genotoxic agent.

In one embodiment, the method further comprises contacting a sample with a ligand which binds to human FANCD2 of SEQ ID NO:1. The ligand is associated with a label which provides a detectable signal. In one embodiment, the ligand is an antibody. The detectable label can be attached to the antibody. Alternatively, the label is attached to a second ligand, which binds to the first ligand. The second ligand can be an antibody. The detectable label can be selected from the group consisting of colorimetric, chemiluminescent, fluorescent, electrochemical labels and combinations thereof. In a preferred embodiment, the label is a fluorescent dye. In one embodiment, detection comprises fluorescence microscopy.

The invention also features a method of testing a patient's sensitivity to a genotoxic agent, comprising the following steps: exposing a patient to a low dose of genotoxic agent; and, detecting the presence of FANCD2-containing foci relative to a control sample. Presence of foci formation relative to a control sample is indicative of a difference in sensitivity of the patient to genotoxic agent. The degree of foci formation relative to a control sample is indicative of the sensitivity of the patient to genotoxic agent. The sample can be selected from a group consisting of peripheral blood, saliva, urine, a cell scraping, exudate, a buccal sample, sputum, and cervical scraping.

In one embodiment, the method further comprises contacting a sample with a ligand which binds to human FANCD2 of SEQ ID NO:1. The ligand is associated with a label which provides a detectable signal. In one embodiment, the ligand is an antibody. The detectable label can be attached to the antibody. Alternatively, the label is attached to a second ligand, which binds to the first ligand. The second ligand can be an antibody. The detectable label can be selected from the group consisting of colorimetric, chemiluminescent, fluorescent, electrochemical labels and combinations thereof. In a preferred embodiment, the label is a fluorescent dye. In one embodiment, detection comprises fluorescence microscopy.

In another aspect, the invention provides for a method of determining the level of DNA damage caused by exposure of subject to a genotoxic agent, comprising the following steps: collecting a sample from the patient following the exposure; and detecting the presence of FANCD2-containing foci relative to a control sample. A difference in foci formation relative to the control sample is indicative of a difference in DNA damage in response to the exposure, and the degree of foci formation relative to a control sample is indicative of a different extent of DNA damage in response to the exposure. The sample can be selected from a group consisting of peripheral blood, saliva, urine, a cell scraping, exudate, a buccal sample, sputum, and cervical scraping.

In another aspect, the invention provides for a method of determining the sensitivity of a sample towards genotoxic agents, comprising the following steps: collecting a sample from the patient, exposing the sample or tissue to a genotoxic agent, and detecting the presence of FANCD2-containing foci relative to a control sample. A difference in foci formation relative to the control sample is indicative of a difference in DNA damage in response to the exposure, and the degree of foci formation relative to a control sample is indicative of a different sensitivity of the tissue towards the agent. The sample can be tumor sample collected from a living subject. In one embodiment, the genotoxic agent can be selected from the group consisting of ionizing radiation or cisplatin. In another embodiment, samples are taken from the living subject at different times to monitor the change in the sensitivity of the sample towards the genotoxic agent.

In one embodiment, the method further comprises contacting a sample with a ligand which binds to human FANCD2 of SEQ ID NO:1. The ligand is associated with a label which provides a detectable signal. In one embodiment, the ligand is an antibody. The detectable label can be attached to the antibody. Alternatively, the label is attached to a second ligand, which binds to the first ligand. The second ligand can be an antibody. The detectable label can be selected from the group consisting of calorimetric, chemiluminescent, fluorescent, electrochemical labels and combinations thereof. In a preferred embodiment, the label is a fluorescent dye. In one embodiment, detection comprises fluorescence microscopy.

In another aspect of the invention, an isolated polynucleotide is provided which comprises a DNA sequence encoding the human FACD2 protein of SEQ ID NO:1 fused in frame with a DNA sequence encoding a fluorescent protein. The polynucleotide can further comprise an expression control sequence operatively linked to the sequence encoding the FANCD2 protein fused in frame with a DNA sequence encoding a fluorescent protein. The fluorescent protein can be selected from the group including: GFP, YFP, CFP, eGFP, eYFP, eCFP, RFP.

In another aspect, the invention provides the protein encoded by an isolated polynucleotide which comprises a DNA sequence encoding the human FACD2 protein of SEQ ID NO:1 fused in frame with a DNA sequence encoding a fluorescent protein. The polynucleotide can further comprise an expression control sequence operatively linked to the sequence encoding the FANCD2 protein fused in frame with a DNA sequence encoding a fluorescent protein. The fluorescent protein can be selected from the group including: GFP, YFP, CFP, eGFP, eYFP, eCFP, RFP.

In yet another aspect, the invention provides a cell expressing an isolated polynucleotide which comprises a DNA sequence encoding the human FACD2 protein of SEQ ID NO:1 fused in frame with a DNA sequence encoding a fluorescent protein. The polynucleotide can further comprise an expression control sequence operatively linked to the sequence encoding the FANCD2 protein fused in frame with a DNA sequence encoding a fluorescent protein. The fluorescent protein can be selected from the group including: GFP, YFP, CFP, eGFP, eYFP, eCFP, RFP.

In another aspect, the invention provides an isolated polynucleotide comprising a DNA sequence encoding a protein that binds with FANCD2 upon foci formation, fused in frame with a DNA sequence encoding a second fluorophore. The nucleic acid encoding a protein that binds with FANCD2 upon foci formation can be selected from the group including: Histone 2AX, BRCA1, and NBS1. The polynucleotide can further comprise an expression control sequence operatively linked to the sequence encoding a protein that binds with FANCD2 upon foci formation, fused in frame with a DNA sequence encoding a second fluorophore. The fluorescent protein can be selected from the group including: GFP, YFP, CFP, eGFP, eYFP, eCFP, RFP. The polynucleotide may further comprise sequence encoding a protein linker sequence.

In yet another embodiment, the invention provides a protein encoded by the isolated polynucleotide comprising a DNA sequence encoding a protein that binds with FANCD2 upon foci formation, fused in frame with a DNA sequence encoding a second fluorophore. The nucleic acid encoding a protein that binds with FANCD2 upon foci formation can be selected from the group including: Histone 2AX, BRCA1, and NBS1. The polynucleotide can further comprise an expression control sequence operatively linked to the sequence encoding a protein that binds with FANCD2 upon foci formation, fused in frame with a DNA sequence encoding a second fluorophore. The fluorescent protein can be selected from the group including: GFP, YFP, CFP, eGFP, eYFP, eCFP, RFP. The polynucleotide may further comprise sequence encoding a protein linker sequence.

In yet another embodiment, the invention provides a cell expressing the isolated polynucleotide comprising a DNA sequence encoding a protein that binds with FANCD2 upon foci formation, fused in frame with a DNA sequence encoding a second fluorophore. The nucleic acid encoding a protein that binds with FANCD2 upon foci formation can be selected from the group including: Histone 2AX, BRCA1, and NBS1. The polynucleotide can further comprise an expression control sequence operatively linked to the sequence encoding a protein that binds with FANCD2 upon foci formation, fused in frame with a DNA sequence encoding a second fluorophore. The fluorescent protein can be selected from the group including: GFP, YFP, CFP, eGFP, eYFP, eCFP, RFP. The polynucleotide may further comprise sequence encoding a protein linker sequence.

In one embodiment, the invention provides a cell expressing the isolated polynucleotide a DNA sequence encoding the human FACD2 protein of SEQ ID NO:1 fused in frame with a DNA sequence encoding a first fluorescent protein and isolated polynucleotide comprising a DNA sequence encoding a protein that binds with FANCD2 upon foci formation, fused in frame with a DNA sequence encoding a second fluorescent protein. The second fluorescent protein is preferably different from the first fluorescent protein. The polynucleotide may further comprise sequences encoding a protein linker sequences. The polynucleotides may further comprise expression control sequences operatively linked to the sequence encoding the proteins fused in frame with the DNA sequence encoding a fluorescent protein. The fluorescent proteins can be selected from the group including: GFP, YFP, CFP, eGFP, eYFP, eCFP, RFP. In a preferred embodiment, the fluorescent proteins are eCFP and eYFP.

In yet another aspect, the invention provides a method of screening test agents which modulate formation of FANCD2-containing foci, comprising the following steps: contacting a biological sample with test compound; and detecting the presence of FANCD2 in FANCD2-containing foci relative to a control sample. A difference in the degree of foci formation relative to a control sample is indicative of an agent active in foci formation. The method may further comprise exposing biological sample to a genotoxic agent.

In one embodiment, the method further comprises contacting the biological sample with a ligand which binds to FANCD2. The ligand is associated with a label which provides a detectable signal. In one embodiment, the ligand is an antibody. The detectable label can be attached to the antibody. Alternatively, the label is attached to a second ligand, which binds to the first ligand. The second ligand can be an antibody. The detectable label can be selected from the group consisting of calorimetric, chemiluminescent, fluorescent, electrochemical labels and combinations thereof. In a preferred embodiment, the label is a fluorescent dye. In one embodiment, detection comprises fluorescence microscopy.

In another embodiment, the method further comprises detecting foci formation using a cell expressing an isolated polynucleotide which comprises a DNA sequence encoding the human FACD2 protein of SEQ ID NO:1 fused in frame with a DNA sequence encoding a fluorescent protein. The polynucleotide can further comprise an expression control sequence operatively linked to the sequence encoding the FANCD2 protein fused in frame with a DNA sequence encoding a fluorescent protein. The fluorescent protein can be selected from the group including: GFP, YFP, CFP, eGFP, eYFP, eCFP, RFP. In one embodiment, foci are detected using fluorescence microscopy.

In yet another embodiment, the method further comprises detecting foci formation using a cell expressing the isolated polynucleotide a DNA sequence encoding the human FACD2 protein of SEQ ID NO:1 fused in frame with a DNA sequence encoding a first fluorescent protein and isolated polynucleotide comprising a DNA sequence encoding a protein that binds with FANCD2 upon foci formation, fused in frame with a DNA sequence encoding a second fluorescent protein. The second fluorescent protein is preferably different from the first fluorescent protein. The polynucleotides may further comprise sequences encoding a protein linker sequences. The polynucleotides may further comprise expression control sequences operatively linked to the sequence encoding the proteins fused in frame with the DNA sequence encoding a fluorescent protein. The fluorescent proteins can be selected from the group including: GFP, YFP, CFP, eGFP, eYFP, eCFP, RFP. In a preferred embodiment, the fluorescent proteins are eCFP and eYFP. In another embodiment, foci are detected be measuring fluorescence resonance energy transfer.

In another aspect, the invention provides a method of protecting a living subject from damage caused by genotoxic agents, the method comprising administering a therapeutically effective amount of an enhancer of FANCD2-containing foci formation to a living subject, such that formation of FANCD2-containing foci formation is enhanced in the living subject when compared to a reference or control. In one embodiment, the enhancer comprises desferrioxamine.

In yet another aspect, the invention provides an antibody that binds to a monoubiquitinated form of FANCD2 polypeptide. Preferably, the antibody binds the monoubiquitinated and not the unubiquitinated form of FANCD2 polypeptide. The antibody may be polyclonal. Alternatively, the antibody may be monoclonal.

In another aspect, the invention provides for a kit for detecting the presence or absence of FANCD2-containing foci in a sample from a live subject comprising the antibody that binds to a monoubiquitinated form of FANCD2, and packaging material. The kit may further comprise a fluorescently labeled secondary antibody, wherein the secondary antibody binds to the first antibody.

Other aspects and advantages of the present invention are described further in the following detailed description of the preferred embodiments thereof.

BRIEF DESCRIPTION OF THE DRAWINGS

FIG. 4. Isolation of a PD20F fibroblast clone, expressing a physiologic level of the GFP-FANCD2 protein and suitable for high throughput drug screening. A subclone (clone 7) was isolated, by limiting dilution, which expresses GFP-FANCD2 protein. Activation of this clone with ionizing radiation (IR) results in the assembly of bright green foci, reading detectable in the fluorescence background of the cell nucleus.

DETAILED DESCRIPTION

Figure 1:
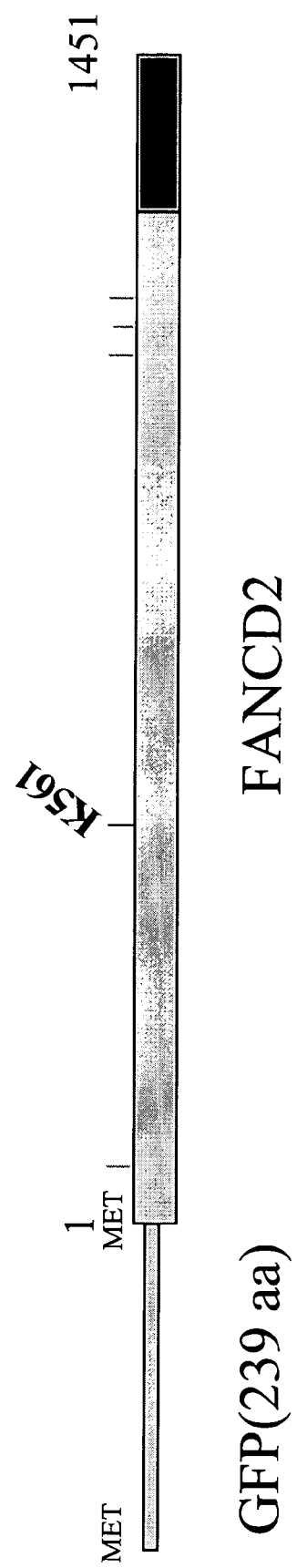
FIG. 1. Schematic model of the GFP (Green Fluorescent Protein) fusion to FANCD2. A cDNA, encoding GFP-fused directly to the amino terminal methionine (MET) of FANCD2, was generated. Transfection of mammalian cells with this cDNA results in expression of the fusion protein, which functions in a reporter assay.

The invention is based upon the observation that FANCD2-containing foci are formed in cells in response to exposure to genotoxic agents. Detection of FANCD2-containing foci in samples from living subjects, therefore, may be used to measure exposure of the subject to such genotoxic agents.

In order to more clearly and concisely describe and point out the subject matter of the claimed invention, the following definitions are provided for specific terms which are used in the following written description and the appended claims.

Definitions

A "genotoxic agent" or "genotoxin" refers to any chemical compound or treatment method that induces DNA damage when applied to a cell. Such agents can be chemical or radioactive. A genotoxic agent is one for which a primary biological activity of the chemical (or a metabolite) is alteration of the information encoded in the DNA. Genotoxic agents can vary in their mechanism of action, and can include: alkylating agents such as ethylmethane sulfonate (EMS), nitrosoguanine and vinyl chloride; bulky addition products such as benzo(a)pyrene and aflatoxin B1; reactive oxygen species such as superoxide, hydroxyl radical; base analogs such as 5-bromouracil; intercalating agents such as acridine orange and ethidium bromide. A variety of chemical compounds, also described as "chemotherapeutic agents," function to induce DNA damage. Chemotherapeutic agents contemplated to be of use include, e.g., adriamycin, 5-fluorouracil (5FU), etoposide (VP-16), camptothecin, actinomycin-D, mitomycin C, cisplatin (CDDP) and even hydrogen peroxide. "Genotoxic agents" also include radiation and waves that induce DNA damage such as γ-irradiation, X-rays, UV-irradiation, microwaves, electronic emissions, and the like. In addition, certain chemicals, sometimes called indirect genotoxic agents, can be converted into genotoxic agents by normal metabolic enzymes. As used herein, genotoxic agents refer to both direct and indirect genotoxic agents. Genotoxic agents cause mutations in DNA, and can cause cancer. The term "genotoxic agents" also encompasses the use of a combination of one or more DNA damaging agents, whether radiation-based or actual compounds.

Because of the wide diversity of genotoxic agents, exposure to genotoxic agents comes in many different forms. Mechanism of exposure to chemical genotoxic agents may include direct contact, or inhalation by the subject. In the case of radiation, exposure may arise from proximity to a source of ionizing radiation. The nature of exposure to these genotoxic agents can also vary. Exposure can be deliberate, as is the case with chemotherapy and radiotherapy, but may also be accidental. Examples of accidental exposure may include occupational chemical exposure in a laboratory, factory or farm, or occupational exposure to ionizing radiation in a nuclear power plant, clinic, laboratory, or by frequent airplane travel.

"DNA damage", as used herein, refers to chemical and/or physical modification of the DNA in a cell, including methylation, alkylation double-stranded breaks, cross-linking, thymidine dimers caused by ultraviolet light, and oxidative lesions formed by oxygen radical binding to DNA bases.

A "ligand" of a protein includes a substrate and other compounds that bind to the protein. In one embodiment, a "ligand" is an antibody that binds to FANCD2. The term "antibody to FANCD2", or "antibody that binds to FANCD2", as used herein, refers to an immunoglobulin molecule which is able to specifically bind to FANCD2. Antibodies can be intact immunoglobulins derived from natural sources or from recombinant sources, or immunoreactive portions of intact immunoglobulins. Antibodies are typically tetramers of immunoglobulin molecules. The antibodies in the present invention exist in a variety of forms including, for example, high affinity polyclonal antibodies, monoclonal antibodies, synthetic antibodies, chimeric antibodies, recombinant antibodies and humanized antibodies. Such antibodies originate from immunoglobulin classes IgG, IgM, IgA, IgD and IgE. The term antibody also includes synthetic antibodies which are generated using recombinant DNA technology, such as, for example, an antibody expressed by a bacteriophage. In one embodiment, a desirable ligand is a monoclonal antibody which binds to monoubiquitinated FANCD2, for example as described in detail in Example 1. Other such antibodies include a Fab, Fab' or F(ab')2, or Fc antibody fragment thereof which binds FANCD2. The invention also provides for a ligand that is a single chain Fv antibody fragment which binds FANCD2.

Another useful "ligand" is a recombinant construct comprising a complementarity determining region of an antibody, a synthetic antibody or a chimeric antibody construct which shares sufficient CDRs to retain the functionally equivalent binding characteristics of an antibody that binds FANCD2.

The term "antibody" includes an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, "immunological methods" means any assay involving antibody-based detection techniques well-known in the art, including, without limitation, Western blotting, immunoprecipitation, FACS analysis, immunofluorescence microscopy, immunohistochemistry and direct and competitive ELISA and RIA techniques (Harlow et al., 1989, Antibodies: A Laboratory Manual, Cold Spring Harbor, N.Y.; Ausubel et al., 1995, Current Protocols in Molecular Biology, John Wiley & Sons, Inc., New York; Sambrook et al., 1989, Molecular Cloning: A Laboratory Manual, Cold Spring Harbor Laboratory Press).

As used herein, "subject" refers to an animal including mammal, and including human, cow, mouse, rat, pig, and sheep. The subject may be of any age or developmental stage. Furthermore, the subject may be healthy, diseased, or contain mutations within its genome. The subject may also have been previously exposed to a genotoxic agent, a therapeutic agent or a test agent. Furthermore, non-human subjects may additionally include transgenic animals. In particular, the subject may carry transgenes or mutations which alter the organism's sensitivity to genotoxic agents.

By "sample" is meant any cell or tissue, or cell or tissue-containing composition or isolate derived from the subject. The sample may be derived from heart, brain, placenta, liver, skeletal muscle, kidney, pancreas, spleen, thymus, prostate, testis, uterus, small intestine, or colon. Another type of biological sample may be a preparation containing white blood cells, e.g., peripheral blood, sputum, saliva, urine, etc. for use in detecting the presence or absence of DNA damage in a subject that has been exposed to a genotoxic agent, such as radiation, chemicals, etc.

As used in the first aspect of the invention, a "control sample" refers to a sample isolated in the same way as the sample to which it is compared, except that the control sample is not exposed to a genotoxic agent.

As used herein, a "reference sample" refers to a sample from a subject that is distinct from the test subject and isolated in the same way as the sample to which it is compared, and which has been exposed to a known quantity of the same genotoxic agent. The subject of the reference sample may be genetically identical to the test subject, or may be different. In addition, the reference sample may be derived from several subjects who have been exposed to a known quantity of the same genotoxic agent.

By "difference in foci formation" is meant an increase or decrease in the number, size or persistence of FANCD2-containing foci, when comparing a test sample with either a control sample or reference sample. A difference includes an increase or decrease that is 2-fold or more, or less, for example 5, 10, 20, 100, 1000-fold or more as compared to a control or reference sample. A difference also includes an increase or decrease that is 5% more or less, for example, 10%, 20%, 30%, 50%, 75%, 100%, as compared to a control or reference sample.

As used herein, exposure to a "low level" of a genotoxic refers to exposure to a dose of a particular genotoxic agent which results in no more than 20% of the maximal number of FANCD2-containing foci in biological samples. Because of the multitude of genotoxic agents to which a sample may be exposed, as well as the varying sensitivities of different samples to such genotoxic agents, it is preferable to express the dosage relative to the formation of FANCD2-containing foci, rather than in the absolute dose of a particular genotoxic agent.

As used herein, "FANCD2-containing foci" are protein complexes comprising FANCD2 which form within nuclei of cells upon exposure to genotoxic agents such as ionizing radiation, or alkylating reagents. FANCD2-containing foci may also contain several other DNA damage response proteins, including Histone 2AX, BRCA1, RAD51, BRCA2, and NBS1. Recent studies suggest that, for ionizing radiation inducible foci, the Histone 2AX protein enters the foci early, followed by BRCA1 and NBS1, followed by FANCD2. The relative speed of foci formation, the duration of foci, and the composition of foci (i.e., which proteins interact with FANCD2) may correlate with different kinds of genotoxic stress (i.e., IR versus alkylating agent versus crosslinker stress).

As used herein, a "protein associated with FANCD2-containing foci" refers to a protein which associates with FANCD2 specifically upon formation of FANCD2-containing foci. These proteins, which include the BRCA1 and NBS1 proteins, show interaction with FANCD2 in FANCD2-containing foci, which form upon DNA damage. At this time, little is known about the nature of the binding interactions among these proteins. Many of the proteins may bind indirectly, through intermediate proteins and post-translational modifications.

By "detecting FANCD2-containing foci" is meant detecting FANCD2 within foci which contain FANCD2. FANCD2 is monoubiquitinated prior to association within foci. Therefore, in addition to immunological methods including immunofluorescence detection of foci using ligands which bind to FANCD2, "detecting FANCD2-containing foci" includes detection of monoubiquitinated FANCD2 in an extract from a sample using ligands which specifically bind to the monoubiquitinated, but not the unubiquitinated, form of FANCD2 using immunological methods. Finally, detecting FANCD2-containing foci can also comprise detecting FANCD2 within FANCD2-containing foci through the use of a FANCD2 protein which is associated with a detectable label, for example, FANCD2 protein fused to a fluorescent protein. FANCD2-containing foci can be detected as early as 30 minutes after exposure to genotoxic stress. However, FANCD2 foci appear to reach a maximum between 8 and 24 hours after exposure.

As used herein, "sensitivity" of a subject to a genotoxic agent refers to the response of an individual subject to a defined dose of a genotoxic agent. A subject is considered sensitive to a genotoxic agent when the subject's DNA is at least 50% more susceptible to damage, for example 55%, 60%, 75%, 100% over a specified time period, or 2-fold or more susceptible to damage, for example, 5-fold, 10-fold, 25-fold, 50-fold, 100-fold or 1000-fold more susceptible over a specified time period, compared with a normal subject. DNA damage can be measured in terms of the number of mutations, double-stranded breaks, or any other means known in the art.

By "degree of foci formation" refers to the total number or the rate of formation of FANCD2-containing foci in a sample. The degree of foci formation can be normalized from one sample to another, for example, to total number of cells, total number of intact nuclei, total sample volume, or total sample mass. As used herein, a cell nucleus is considered "positive for FANCD2-containing foci" if there are greater than five bright foci in the nucleus.

"Modulate" formation of FANCD2-containing foci, as used herein, refers to a change or an alteration in the formation of FANCD2-containing foci in a biological sample. Modulation may be an increase or a decrease in foci number, size or persistence within a biological sample, and includes an increase or decrease that is 2-fold or more, or less, for example 5, 10, 20, 100, 1000-fold or more as compared to a control or reference sample. Modulation may also be an increase or decrease that is 5% more or less, for example, 10%, 20%, 30%, 50%, 75%, 100%, as compared to a control or reference sample.

The term "modulator" refers to a chemical compound (naturally occurring or non-naturally occurring), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. Modulators are evaluated for potential activity as inhibitors or activators (directly or indirectly) of a biological process or processes (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in screening assays described herein. The activities (or activity) of a modulator may be known, unknown or partially-known. Such modulators can be screened using the methods described herein.

The term "candidate modulator" refers to a compound to be tested by one or more screening method(s) of the invention as a putative modulator. Usually, various predetermined concentrations are used for screening such as 0.01 µM, 0.1 µM, 1.0 µM, and 10.0 µM, as described more fully below. Test compound controls can include the measurement of a signal in the absence of the test compound or comparison to a compound known to modulate the target.

As used herein, an "enhancer" of FANCD2-containing foci formation refers to a chemical compound which causes an increase in the formation of FANCD2-containing foci in a living subject or a biological sample. Enhancement may be an increase in number, size or persistence of FANCD2-containing foci, and includes an increase that is 2-fold or more, for example, 2, 5, 10, 20, 100, 1000-fold or more as compared to a control or reference. Enhancement may also be an increase of 5% or more, for example 5%, 10%, 20%, 30%, 50%, 75%, 100% or more, as compared to a control or reference.

As used herein, an "inhibitor" of FANCD2-containing foci formation refers to a chemical compound which causes a decrease in the formation of FANCD2-containing foci in a living subject or a biological sample. Inhibition may be a decrease in number, size or persistence of FANCD2-containing foci, and includes a decrease that is 2-fold or more, for example, 2, 5, 10, 20, 100, 1000-fold or more as compared to a control or reference. Inhibition may also be an decrease of 5% or more, for example 5%, 10%, 20%, 30%, 50%, 75%, or up to 100%, as compared to a control or reference.

A "fusion protein" is a protein that contains at least two polypeptide regions and, optionally, a linking peptide that operatively link the two polypeptides into one continuous polypeptide. The at least two polypeptide regions in a fusion protein are derived from different sources, and therefore a fusion protein comprises two polypeptide regions not normally joined together in nature. The at least two polypeptides can be joined in any order.

A "linking sequence (or linker peptide)" contains one or more amino acid residues joined via peptide bonds. A linking sequence serves to join two polypeptide regions of differing origins in a fusion protein via a peptide bond between the linking sequence and each of the polypeptide regions. Preferably, a length of linking sequence is between 1 and 20 amino acids in length, and more preferably between 3 and 10 amino acids in length.

Typically, a fusion protein is synthesized as a continuous polypeptide in a recombinant host cell which contains an expression vector comprising a nucleotide sequence encoding the fusion protein wherein the different regions of the fusion protein are fused in frame on either side of a linker peptide's coding sequence. The chimeric coding sequence (encoding the fusion protein) is operatively linked to expression control sequences (generally provided by the expression vector) that are functional in the recombinant host cell.

The term "vector" or "expression vector" refers to a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

"Operatively-linked" refers to polynucleotide sequences which are necessary to effect the expression of coding and non-coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, components whose presence can influence expression, and can also include additional components whose presence is advantageous, for example, leader sequences and fusion partner sequences.

As used herein, a "pharmaceutical composition" comprises a pharmacologically effective amount of a modulator of FANCD2-containing foci formation and a pharmaceutically acceptable carrier. As used herein, "pharmacologically effective amount," "therapeutically effective amount" or simply "effective amount" refers to that amount of a modulator of FANCD2-containing foci formation, effective to produce the intended pharmacological, therapeutic or preventive result. For example, if a given clinical treatment is considered effective when there is at least a 25% enhancement in foci formation, a therapeutically effective amount is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

The term "pharmaceutically acceptable salt" refers to both acid addition salts and base addition salts. The nature of the salt is not critical, provided that it is pharmaceutically acceptable. Exemplary acid addition salts include, without limitation, hydrochloric, hydrobromic, hydroiodic, nitric, carbonic, sulphuric, phosphoric, formic, acetic, citric, tartaric, succinic, oxalic, malic, glutamic, propionic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric, galacturonic acid and the like. Suitable pharmaceutically acceptable base addition salts include, without limitation, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine, procaine and the like. Additional examples of pharmaceutically acceptable salts are listed in *Journal of Pharmaceutical Sciences* (1977) 66:2. All of these salts may be prepared by conventional means from a modulator of FANCD2-containing foci by treating the compound with the appropriate acid or base.

FANCD2 Foci

The cellular response to DNA damage is a complex interacting network of pathways that mediate cell cycle checkpoints, DNA repair, and apoptosis. A model lesion for the investigation of these pathways has been DNA double-strand breaks, which rapidly induce cell cycle checkpoints and are repaired by a number of different pathways. In mammalian cells, both homologous recombination and nonhomologous recombination pathways are utilized. Extensive studies in mammalian cells have shown that complexes of DNA repair and cell cycle checkpoint proteins rapidly localize to sites of double-strand breaks induced by ionizing radiation. These proteins create foci that can be detected by immunofluorescent analyses.

The Fanconi anemia complementation group D2 (FANCD2) is a component of a protein complex involved in chromosome stability and repair. Fanconi anemia (FA) is a hereditary disorder characterized, in part, by a deficient DNA-repair mechanism that increases a person's risk for a variety of cancers. In response to DNA damage, the FA complex activates FANCD2, which then associates with BRCA1. Activation of FANCD2 occurs by phosphorylation of a serine 222 residue by the ATM kinase. In addition, activation via the FA pathway occurs via monoubiquitination of FANCD2 at lysine 561. In its unmodified form, FANCD2 is diffusely located throughout the nucleus. When ubiquitinated, FANCD2 forms dots, or foci, in the nucleus. The ubiquitination of FANCD2 and subsequent formation of nuclear foci occurs in response to DNA damage. By coimmunoprecipitation, Nakanishi et al. (2002) found constitutive interaction between FANCD2 and NBS1, and they provided evidence that these proteins interact in two distinct assemblies to mediate S-phase checkpoint and resistance to mitomycin C-induced chromosome damage.

At least two types of ionizing radiation-induced foci have been observed: one containing the Rad51, BRCA1 and BRCA2 proteins, and another containing the Mre11-Rad50-NBS1 complex. Rad51 foci, which contain the tumor suppressor proteins BRCA1 and BRCA2, also appear during S phase in the absence of exogenous induction of DNA damage.

Mre11-Rad50-NBS1 foci can be detected as early as 10 min after irradiation and are clearly present at sites of DNA breaks, while DNA repair is ongoing. These foci also colocalize with the BRCA1 protein, which has been shown to be required for their formation, possibly through its physical interaction with human Rad50 (hRad50). In addition, coimmunoprecipitation experiments performed with BRCA1 have indicated the presence of a large number of additional proteins in this complex (referred to as the BRCA1-associated surveillance complex). These include the mismatch repair proteins Msh2, Msh6, and Mlh1, the checkpoint kinase ATM, the product of the Bloom's syndrome gene BLM, and replication factor C. BRCA1, NBS1, and hMre11 have all been shown to be substrates of the ATM kinase and to become phosphorylated in response to the presence of DNA breaks.

The present invention is related to the discovery that cells exposed to genotoxic agents form FANCD2-containing foci. Multiple DNA damage response proteins have now been identified which form nuclear foci, also called IRIFs (Ionizing-Radiation Inducible foci) in response to DNA damage.

Dosage- and Time-Dependence of Foci Formation in Response to Genotoxic Agent

In vitro studies show that cellular exposure to Ionizing Radiation (in the 0.5 to 5 Gy range) results in a dose-dependent increase in FANCD2 monoubiquitination and foci formation. Foci can be detected as early as 30 minutes after IR exposure, and peak foci are observed between 8 and 24 hours after exposure. Foci formation is delayed (compared to this IR response) after cellular exposure to toxic drugs, such as cisplatin and mitomycin C (MMC). This delay probably reflects the slow uptake of these drugs and the requirement for metabolic activation before the DNA is actually damaged. Importantly, these studies have been done in vitro.

Ligands According to the Invention

Ligands useful for the invention includes antibodies that bind to FANCD2. Antibodies that bind to FANCD2 have been described (US20030093819A1; Garcia-Higuera et al., 2001. Mol. Cell. 7:249-62). Alternatively antibodies that bind to FANCD2 can be generated by conventional means utilizing the isolated, recombinant or modified FANCD2 or fragments thereof as antigens of this invention. For example, polyclonal antibodies are generated by conventionally stimulating the immune system of a selected animal or human with a FANCD2 antigen, allowing the immune system to produce natural antibodies thereto, and collecting these antibodies from the animal or human's blood or other biological fluid. Preferably a recombinant version of FANCD2 is used as an immunogen. Monoclonal antibodies (MAbs) directed against FANCD2 are also generated conventionally. Hybridoma cell lines expressing desirable MAbs are generated by well-known conventional techniques, e.g. Kohler and Milstein and the many known modifications thereof. Similarly desirable high titer antibodies are generated by applying known recombinant techniques to the monoclonal or polyclonal. antibodies developed to these antigens [see, e.g., PCT Patent Application No. PCT/GB85/00392; British Patent Application Publication No. GB218863 8A; Amit et al., 1986 Science, 233:747-753; Queen et al., 1989 Proc. Nat'l. Acad. Sci. USA, 86:10029-10033; PCT Patent Application No. PCT/WO9007861; and Riechmann et al., Nature, 332:323-327 (1988); Huse et al, 1988 a Science, 246:1275-1281].

Given the disclosure contained herein, one of skill in the art generates ligands or antibodies directed against FANCD2 by techniques known in the art, for example, by manipulating the complementarity determining regions of animals or human antibodies to the antigen of this invention. See, e.g., E. Mark and Padlin, "Humanization of Monoclonal Antibodies", Chapter 4, The Handbook of Experimental Pharmacology, Vol. 113, The Pharmacology of Monoclonal Antibodies, Springer-Verlag (June, 1994); Harlow et al, 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al, 1988, Proc. Natl. Acad. Sci. USA 85:5879-5883; and Bird et al, 1988, Science 242:423-426.

Alternatively, FANCD2 antigens are assembled as multi-antigenic complexes [see, e.g., European Patent Application 0339695, published Nov. 2, 1989] and employed to elicit high titer antibodies capable of binding the FANCD2. The present invention also provides anti-idiotype antibodies (Ab2) and anti anti-idiotype antibodies (Ab3). Ab2 are specific for the target to which anti-FANCD2 antibodies of the invention bind and are similar to FANCD2 antibodies in their binding specificities and biological activities [see, e.g., M. Wettendorff et al., "Modulation of anti-tumor immunity by anti-idiotypic antibodies." In Idiotypic Network and Diseases, ed. by J. Cerny and J. Hiernaux, 1990 J 4177. Soc. Microbiol., Washington D.C.: pp. 203-229]. These anti-idiotype and anti-anti-idiotype antibodies are produced using techniques well known to those of skill in the art. Such anti-idiotype antibodies (Ab2) can bear the internal image of FANCD2 and are thus useful for the same purposes as FANCD2.

In general, polyclonal antisera, monoclonal antibodies and other antibodies which bind to FANCD2 as the antigen (Ab1) are useful to identify epitopes of FANCD2 to separate FANCD2 and its analogs from contaminants in living tissue (e.g., in chromatographic columns and the like), and in general, as research tools and as starting material essential for the development of other types of antibodies described above. Anti-idiotype antibodies (Ab2) are useful for binding the same target and thus are used in place of FANCD2 to induce useful ligands to FANCD2. The Ab3 antibodies are useful for the same reason the Ab 1 are useful. Other uses, as research tools and as components for separation of FANCD2 from other contaminants, for example, are also contemplated for the above-described antibodies.

Antibodies that Bind Specifically to Monoubiquitinated FANCD2

The total cellular level of FANCD2 protein does not significantly change in response to DNA damage. Rather, DNA damage results in monoubiquitination of FANCD2, as well as recruitment into FANCD2-containing foci. It will be appreciated by one skilled in the art that an alternative to measuring the presence of FANCD2-containing foci is to use a ligand which specifically binds the monoubiquitinated, but not the unubiquitinated form of FANCD2. To detect the presence of monoubiquitinated FANCD2, the ligand is preferably associated with a detectable label as described above. The main advantage of using such a ligand, as will be appreciated by one skilled in the art, is that, due to the typically low basal level of monoubiquitinated FANCD2 in cells with undamaged DNA, the level of FANCD2-containing foci can be measured in a sample taken from a living subject using the level of monoubiquitinated FANCD2 as a surrogate marker by additional means besides immunofluorescence microscopy. An antibody which specifically recognizes the monoubiquitinated form of FANCD2 (FANCD2-L) has considerable utility as a rapid diagnostic. For instance, this antibody could be used for:

1) Immunohistochemistry (IH). This antibody could be used to examine tissue sections prepared from solid tumors (e.g., breast, ovarian, lung tumors). A positive signal by IH would predict that the tumor will be resistant to cisplatin and related drugs.

2) FACS analysis. Peripheral blood lymphocytes (PBLs) could be screened with this antibody. A positive signal suggests the presence of activated FANCD2, consistent with a recent exposure of an individual to IR. or toxin. Thus, this antibody is a useful extension of the radiation dosimeter assay described in this application.

3) A high-throughput assay to screen for inhibitors of the purified FA complex (monoubiquitin ligase). These inhibitors will block the ability of the FA complex to monoubiquitinate FANCD2 in vitro. The new monoclonal antibody will be a useful reagent for end product detection. Additional methods of measuring FANCD2-containing foci using a ligand which specifically recognizes monoubiquitinated FANCD2 include immunoblot analysis, or Enzyme linked immunosorbant assays (ELISA) using extracts of samples collected from living subjects, or FACS analysis (Harlow et al, 1999, Using Antibodies: A Laboratory Manual, Cold Spring Harbor Laboratory Press, NY).

A sensitive measure of IR exposure is the increased monoubiquitination of FANCD2. In undamaged cells, the (L/S) ratio of FANCD2-L (monoubiquitinated isoform) to FANCD2-S (unubiquitinated isoform) is approximately 0.5-0.6. This ratio is readily calculated by comparing the density of the L band to the S band on a western blot. A sensitive indicator of increased FANCD2 monoubiquitination and IR exposure is the conversion of the L/S ratio to 1.0 or greater.

Detectable Labels Useful for the Invention

The detectable label useful according to the invention is selected from the group consisting of radioactive, enzymatic, colorimetric, chemiluminescent, fluorescent, electrochemical labels and combinations thereof. In a preferred embodiment of this aspect, the detectable label is a fluorescent compound. In a particularly preferred embodiment, the detectable label is selected from the group consisting of fluorescein, rhodamine, bodipy, cyanine, Alexa, Naphthofluorescein, Oregon Green, coumarin, dansyl, Texas Red, pyrene, Cascade Blue, and Alexa 350 and derivatives thereof. In certain embodiments, fluorescent proteins may be used. For example, green fluorescent proteins (GFPs) of cnidarians, which act as their energy-transfer acceptors in bioluminescence, can be used in the invention. A green fluorescent protein, as used herein, is a protein that fluoresces green light, and a blue fluorescent protein is a protein that fluoresces blue light. GFPs have been isolated from the Pacific Northwest jellyfish, *Aequorea victoria*, from the sea pansy, *Renilla reniformis*, and from *Phialidium gregarium* (Ward et al., 1982, *Photochem. Photobiol.* 35:803-808; Levine et al., 1982, *Comp. Biochem. Physiol.* 72B:77-85).

A preferred fluorescent protein is green fluorescent protein (GFP) or a modified GFP. Wild-type GFP has long been used in the art. Starting from green fluorescent protein, many modified versions have been derived with altered or enhanced spectral properties as compared with wild-type GFP. See, e.g., U.S. Pat. No. 5,625,048; International Patent Publication WO 97/28261; International Patent Publication WO 96/23810. Useful are the modified GFPs W1B and TOPAZ, available commercially from Aurora Biosciences Corp., San Diego, Calif. W1B contains the following changes from the wild-type GFP sequence: F64L, S65T, Y66W7 N1461, M153T, and V163A (see Table 1, page 519, of Tsien, 1998, Ann. Rev. Biochem. 67:509-544). TOPAZ contains the following changes from the wild-type GFP sequence: S65G, V68L, S72A, and T203Y (see Table 1, page 519, of Tsien, 1998, Ann. Rev. Biochem. 67:509-544). Wild-type nucleotide and amino acid sequences of GFP are shown in FIG. 1 and SEQ ID NO: 1 of International Patent Publication WO 97/28261; in FIG. 1 of Tsien, 1998, Ann. Rev. Biochem. 67:509544; and in Prasher et al., 1992, Gene 111:229. Of particular interest in using fluorescent proteins in FRET-based screening assays are variants of the A. Victoria GFP known as Cyan FP (CFP, Donor (D)) and Yellow FP (YFP, Acceptor (A)). As an example, the YFP variant can be made as a fusion protein with FANCD2 polypeptide. Vectors for the expression of GFP variants as fusions (Clontech) as well as flurophore-labeled compounds (Molecular Probes) are known in the art. When expressing GFPs in mammalian cells, it may be advantageous to construct versions of the GFPs having altered codons that conform to those—20 codons preferred by mammalian cells (Zolotukhin et al., J. Virol. 1996, 70:4646-46754; Yang et al., 1996, Nucl. Acids Res. 24:4592-4593). Another way of improving GFP expression in mammalian cells is to provide an optimal ribosome binding site by the use of an additional codon immediately after the starting methionine (Crarneli et al., 1996, Nature Biotechnology 14:315-319).

Diagnostic Methods According to the Invention

A diagnostic method of the invention comprises contacting a sample taken from a living subject, where the sample is preferably immobilized or fixed on a surface such as a microscope slide, with a ligand that binds to human FANCD2. Such ligands are discussed in detail above, and are preferably associated with a detectable label which provides a signal. The sample is then examined for the presence of signal concentrated in nuclear foci of FANCD2 in the cells of the sample. The presence of FANCD2-containing foci in the sample are then detected using immunofluorescence microscopy. In one embodiment, FANCD2 containing foci are detected by detecting a label on a primary antibody that binds to FANCD2. In another embodiment, FANCD2 containing foci are detected by detecting the label of on a secondary antibody or reagent which binds to a primary antibody that binds to FANCD2. The presence of FANCD2-containing foci in a sample is indicative of exposure of the subject to a genotoxic agent, while the presence of diffuse signal is indicative of a lack of DNA damage in the sample. In addition, the number, size, and persistence of FANCD2-containing foci within a sample, as compared to a control sample, are directly proportional to the amount of DNA damage the cell has sustained. The best method to quantify toxin or radiation exposure is to measure the increase in the percentage of cells with five or more bright foci. So, a population of peripheral blood lymphocytes from (unexposed) adult human controls has only 1-2% foci-positive cells (i.e., cells with greater than five FANCD2 foci/cell). Following radiation exposure, there is an increase in the percentage of foci-positive cells (to >10% of the cell population) depending on the dose and site of x-ray exposure.

The formation of foci is known to be time-dependent. It is preferable for the sample to be collected within a relatively short time after exposure or suspected exposure of the subject with a potential genotoxic agent. In a particular embodiment, samples are collected no longer than 7 days after contact exposure. For example, samples are collected 1 hr, 2 hrs, 4 hrs, 6 hrs, 12 hrs, 18 hrs, 24 hrs, 48 hrs, 72 hrs, 96 hrs, 120 hrs, and 144 hrs and 168 hrs. In a particularly preferred embodiment, the samples are collected within 72 hours after exposure. In a most preferred embodiment, the samples are collected between 6 and 48 hours after exposure.

It will be appreciated by those skilled in the art that the presence of a control sample will provide additional uses in quantitation of exposure to genotoxic agents. Thus, in a preferred embodiment of this aspect of the invention, the diagnostic method of this invention further comprises contacting the sample taken from a living subject, where the sample is preferably immobilized or fixed on a surface such as a microscope slide, with a ligand that binds to human FANCD2. The sample is then examined for the presence of signal concentrated in nuclear foci of FANCD2 in the cells of the sample.

The examining step is any suitable assay step, including, without limitation, fluorescent immunofluorescence microscopy or immunohistochemical analysis. The presence of FANCD2-containing foci in a test sample as compared to a control sample is indicative of exposure of the subject to a genotoxic agent, while the presence of diffuse signal is indicative of a lack of DNA damage in the sample. In addition, a difference in the number, size, and persistence of FANCD2-containing foci within a sample relative to control sample is indicative of a difference in DNA damage in response to exposure to a genotoxic agent, and the degree of foci formation relative to a reference sample is indicative of a different extent of DNA damage in response to said exposure.

Pre- and Post-Therapy Diagnostic Methods

The invention provides for further methods for determining the sensitivity of a patient to radiotherapy or chemotherapy. In one embodiment, the diagnostic method comprises exposing a subject or extracted lymphocytes from a subject, prior to chemotherapy or radiotherapy, to a low dose of a genotoxic agent, contacting the sample taken from the living subject with a ligand that binds to human FANCD2, where the sample is preferably immobilized or fixed on a surface such as a microscope slide. Such ligands are discussed in detail above, and are preferably associated with a detectable label which provides a signal, also as discussed above. The sample is then examined for the presence of signal concentrated in nuclear foci of FANCD2 in the cells of the sample. The examining step is any suitable assay step, including, without limitation, immunofluorescence microscopy or immunohistochemical analysis. Reduced formation of FANCD2-containing foci compared to a control indicates radio- or chemoresistance. In contrast, enhanced foci formation may indicate relative radio- or chemosensitivity. Alternatively, samples can be contacted with a ligand which binds specifically to monoubiquitinated FANCD2. Thus, in another embodiment of this aspect of the invention, the diagnostic method of this invention comprises exposing a patient to a low dose of genotoxic agent and detecting the presence of FANCD2-containing foci relative to a control sample, wherein the presence of foci formation relative to a control sample is indicative of a difference in sensitivity of said patient to genotoxic agent.

Additionally, this method can be employed to rapidly and readily assess DNA damage in patients treated with gamma irradiation or other chemotherapeutic agents, particularly those known to cause DNA damage. Therefore, a further embodiment of this invention is a diagnostic method of determining the extent of DNA damage caused by exposure of a subject to therapeutic agent, comprising collecting a sample from said patient following exposure and detecting the presence of FANCD2-containing foci relative to a control sample. A difference in foci formation relative to said control sample is indicative of a difference in DNA damage in response to said exposure, and wherein the degree of foci formation relative to a control sample is indicative of a different extent of DNA damage in response to said exposure.

Diagnostic Methods Using Samples Collected from Subjects

Prior to administering radiation therapy or chemotherapy to a subject who has cancer, it would be advantageous to be able to pre-test a tumor sample to ascertain its sensitivity towards a therapeutic agent such as ionizing radiation or cisplatin. Such a pre-test will ensure that the best mode of therapy is used for the particular cancer. Thus, in one aspect of the invention, a method of determining the sensitivity of a sample towards genotoxic agents is provided, comprising the following steps: collecting a sample from the patient, exposing the sample or tissue to a genotoxic agent, and detecting the presence of FANCD2-containing foci relative to a control sample. The sample can comprise a tumor biopsy taken from a living subject. A difference in foci formation relative to the control sample is indicative of a difference in DNA damage in response to the exposure, and the degree of foci formation relative to a control sample is indicative of a different sensitivity of the tissue towards the agent. Any therapeutic agent which is known to cause genotoxic stress can be tested in this method. Examples of such genotoxic agents include ionizing radiation or cisplatin.

In certain situations, it may be important to monitor the progress of a tumor sample in the subject over a period of time. For example, while a subject is receiving chemotherapy for a tumor, it would be important to determine whether the tumor has developed resistance towards the therapeutic agent. Therefore, in another embodiment, the method further comprises collecting multiple samples from a subject at different time points. These collected samples are exposed to the same genotoxic agent, and are preferably exposed to the same level of the genotoxic agent. FANCD2-containing foci are then detected in these samples using any of the methods previously described. By comparing the FANCD2-containing foci in these samples to control samples, and by further monitoring the change in FANCD2-containing foci in these samples over time, it can be ascertained whether the tissue's sensitivity towards a particular genotoxic agent has changed. For example, a decrease in FANCD2-containing foci over time indicates a loss in sensitivity of the sample towards that particular genotoxic agent.

Drug Screening Methods of the Invention

High throughput screening has been a frequent first step used in industry and academia for the identification of compounds that target specific molecules or cellular processes. As described below, the monitoring of FANCD2 foci in samples, in vitro and in vivo, provides a useful screening tool for new drug discovery. The invention provides for methods for screening for a radioprotective agent.

1) A radioprotective agent may, itself, cause an increase in FANCD2 foci in peripheral blood lymphocytes. By enhancing the baseline level of FANCD2 foci, the radioprotective agent may activate low (baseline) levels of DNA repair. If an individual is treated with a radioprotective agent and is subsequently exposed to a genotoxic agent, an individual may have an increased (primed) DNA repair response, thus leading to enhanced protection from the radiation damage.

2) In another embodiment, a putative radioprotective agent may enhance DNA repair, without increasing FANCD2 foci. FANCD2-containing foci are monitored following exposure to low doses of a genotoxic agent may allow an investigator to assess the relative protective effect of putative agent. For instance, in this case, radioprotection by a novel agent will result in decreased FANCD2 following challenge with a genotoxic agent.

Methods of screening test compounds are described which are useful in identifying compositions that are active in FANCD2-containing foci formation. Such a composition may be useful as a protective agent against a genotoxic agent or as a chemosensitizer. These methods comprise contacting a biological sample with test compound and detecting the presence of FANCD2 foci formation relative to a control sample. A difference in the degree of foci formation relative to a control sample is indicative of an agent active in foci formation.

One embodiment of this method further comprises employing a FANCD2 ligand associated with a detectable label to detect FANCD2-containing foci. In this embodiment, such a screening method is employed to identify agents which inhibit the formation of FANCD2-containing foci. According to this method, a selected biological sample is contacted with a test compound (i.e., the "test sample") as well as an identical sample without test compound (i.e., the "control sample") under conditions which normally result in formation of FANCD2-containing foci, for example, by contact with a genotoxic agent. In this aspect, the level of genotoxic agent is selected such that a relatively high number of foci are reproducibly formed in a control sample. The test sample and control sample are then contacted with a FANCD2 ligand which is associated with a detectable label. Alternatively, samples may be contacted with a ligand which specifically recognizes monoubiquitinated FANCD2. The test sample and control sample are subsequently examined and compared for the presence, number and size of FANCD2-containing foci using methods such as immunofluorescence microscopy. A reduction in, or absence of, FANCD2-containing foci in the test sample relative to the control sample indicates that the test compound is capable of inhibiting the formation of FANCD2-containing foci in this assay. The presence and/or number of foci are indicated by the level or intensity of the signal generated by the label on the ligand. The signal (or its level of expression or intensity) indicates the presence and number of FANCD2-containing foci. When the signals generated by the label in the test sample are compared with the signals (if any) generated by the labels in the control sample, a lesser detectable signal in the test cell indicates that said test compound has inhibited the formation of FANCD2-containing foci in the cell. For example, test samples exhibiting at least 10% less, for example 10%, 20%, 30%, 50%, 75%, or up to 100% less, FANCD2-containing foci when compared to a control sample is indicative of an agent active in inhibiting the formation of FANCD2-containing foci in the cell.

In another aspect of this embodiment, such a screening method is employed to identify agents which enhance the formation of FANCD2-containing foci. Such a method involves contacting a selected biological sample with a test compound (i.e., the "test sample") as well as an identical sample without test compound (i.e., the "control sample"). The test sample and control sample may optionally be exposed to a low level of genotoxic agent. The test sample and control sample are subsequently examined and compared for the presence and number of FANCD2-containing foci using methods described above. An increase of at least 10%, for example 10%, 20%, 30%, 50%, 75%, 100%, 200%, or 500%, in FANCD2-containing foci in the test sample relative to the control sample indicates that the test compound is capable of inducing the formation of FANCD2-containing foci in this assay.

Mutagenicity Testing for FANCD2-Foci Inducing Compounds

Upon identification of such compounds active in formation of FANCD2-containing foci, it will be necessary to determine whether the compounds posses genotoxic activity, or merely induce FANCD2-containing foci without possessing genotoxicity. It will be appreciated by one skilled in the art that genotoxicity can be measured using one of many well-established assays. A comprehensive list of such methods can be found in *Toxicological Principles for the Safety Assessment of Direct Food Additives and Color Additives Used in Food. Draft Redbook II*. Washington, D.C.: CFSAN, Food and Drug Administration, which is also available in electronic form (on the world wide web at www.cfsan.fda.gov/~redbook/redtoca.html). Common methods include the Ames test for mutagenicity (Ames, B. N., McCann, J. & Yamasaki, E. (1975) Methods for detecting carcinogens and mutagens with *Salmonella*/mammalian-microsome mutagenicity test. Mutation Res. 31, 347-364.), chromosome aberration test (Galloway, S. M., Aardema, M. J., Ishidate Jr., M., Ivett, J. L., Kirkland, D. J., Morita, T., Mosesso, P., and Sofuni, T. (1994). Report from working group on in vitro tests for chromosomal aberrations. Mutation Research 312, 241-261), which are incorporated in its entirety by reference.

Briefly, the Ames test is performed using the following procedure. The objective of this assay is to evaluate the mutagenic potential of test chemicals by studying their effect on one or more histidine requiring strains of *Salmonella typhimurium* in the absence and presence of a liver metabolizing system. When the cultures are exposed to a mutagen some of the bacteria undergo genetic changes due to chemical interactions resulting in reversion of the bacteria to a non-histidine-requiring state. The reverted bacteria will then grow in the absence of exogenous histidine thus providing an indication of the potential of the chemical to cause mutation. Multiple tester strains are necessary because different strains are mutated by a different class (or different classes) of compound. Other types of bacteria can also be used, e.g. tryptophan requiring strains of *Escherichia coli*. The basis of the test is very similar, the only difference being that the bacteria have a requirement for a different amino acid. Nutrient broth is inoculated with the appropriate *Salmonella* strain (TA98, TA100, TA1535, TA1537, TA102) and incubated overnight. A dose rangefinder for the test chemical is carried out using strain TA100 only over a wide dose range. Bacterial culture, test chemical and S9 mix (or co-factor solution) are mixed with soft agar and then added to minimal agar plates. The plates are incubated, and inverted in the dark, for 48-72 hours. After this time the number of revertant colonies are counted. An additional two mutation experiments are carried out, with doses chosen on the basis of the rangefinder. The number of colonies are counted from both experiments and the mean is calculated for the individual plate counts for each dose within an experiment. Statistical analysis of the counts are carried out, and the results for mutagenicity are assessed. Compounds tested should ideally form less than 10-fold higher, for example 10-fold, 8-fold, 5-fold, 2-fold, 1-fold higher, revertants at 1 µM of compound when compared to control samples that were not exposed to mutagen.

GFP-FANCD2-Based Screening Methods

In yet another embodiment, a screening method comprises detecting FANCD2-containing foci in cells expressing genetic constructs expressing FANCD2 fused to a reporter fluorescent protein, and using fluorescence microscopy. Recombinant nucleic acid constructs of particular use in the invention include those which comprise in-frame fusions of sequences encoding the human FANCD2 or fragments thereof and a fluorescent protein. Such a nucleic acid molecule encodes a polypeptide comprising FANCD2, fused to a fluorescent protein label and operatively linked to gene regulatory sequences.

This embodiment of the screening method further comprises cells transfected with a recombinant nucleic acid construct encoding the human FANCD2 protein fused to a reporter protein. This embodiment of the screening method differs from the previous embodiment in the method of detection. In this embodiment, FANCD2-containing foci is detected without the need for a FANCD2-binding ligand.

Instead FANCD2-containing foci are detected directly by detecting the reporter protein which is fused to FANCD2.

As taught in Examples 4 and 5, a preferred genetic construct according to this invention employs the enhanced green fluorescent protein (eGFP) fused to the N-terminal methionine of full-length human FANCD2. PD20 cells expressing this genetic construct express the fusion protein which is monoubiquitinated upon exposure of cells to genotoxic agents. Furthermore, the GFP-FANCD2 construct corrects the hypersensitivity of these cells towards genotoxic agents such as Mitomycin C (MMC). Exposure of these cells with genotoxic agents results in formation of FANCD2-containing foci, as visualized by detecting the eGFP fluorescence, obviating the need for ligands which bind FANCD2 or monoubiquitinated FANCD2.

FRET-Based Screening Methods

In a still further embodiment, FANCD2-containing foci are detected in cells expressing two genetic constructs, wherein at least one construct expresses FANCD2 fused to a first reporter fluorescent protein, and a second construct expresses a second protein associated with FANCD2-containing foci fused to a second reporter fluorescent protein, and wherein FANCD2-containing foci are detected by fluorescence resonance energy transfer (FRET). Preferred examples of proteins associated with FANCD2-containing foci include NBS1 (Nakanishi et al., 2002. Nat Cell Biol. 4:913-20) and BRCA1 (Garcia-Higuera et al., 2001. Mol Cell. 7:249-62). In this embodiment, two fluorescent reporter proteins are chosen which serve as acceptor and donor fluorophores. Upon exposure of cells to genotoxic agents, the FANCD2-fluorescent reporter fusion protein and either the NBS1-fluorescent reporter fusion protein or BRCA1-fluorescent reporter fusion protein associate to form FANCD2-containing foci. In one embodiment, constructs are generated, one of which encodes FANCD2 fused with a donor fluorescent protein such as the cyan variant of GFP (CFP). Another construct is generated which encodes the acceptor fluorescent protein, preferably the yellow variant of GFP (YFP), fused with a foci-associated protein selected from the group consisting of NBS1, Histone 2AX, and BRCA1. These constructs are operatively linked with promoter and terminator sequences in a vector as described previously, or by employing methods well known in the art. The two fluorescent protein fusion constructs can be placed on separate vectors or on the same vector. A host cell is then transformed such that both constructs are expressed. Expression of both constructs can be tested by detecting fluorescence of CFP and YFP in the presence or absence of exposure to genotoxic agents using methods known in the art, for example by fluorescence microscopy at the appropriate wavelengths.

The physical proximity of the two fluorescent proteins results in increased fluorescence resonance energy transfer, which can be detected using fluorescent methods, including FRET microscopy, ratio imaging, or ratiometric fluorimetry. An instrument such as FLIPR™ can be set to alternate between reading signals at two different wavelengths with a cycling time of about one second, and is therefore extremely useful in measuring samples in high-throughput.

Fluorescence resonance energy transfer (FRET) is a non-radiative process whereby energy from a fluorescent donor molecule is transferred to an acceptor molecule without the involvement of a photon. Excitation of the donor molecule enhances the fluorescence emission of the longer-wavelength acceptor molecule (i.e., sensitized acceptor emission). The quantum yield of the donor fluorescence emission is concomitantly diminished. FRET has become a valuable tool for microscopy, because the efficiency of energy transfer has a strong inverse dependence on the distance between the donor and acceptor molecules. Thus, the appearance of FRET is a highly specific indicator of the proximity of the two molecules. This has led to the use of FRET efficiency as a "spectroscopic ruler" to measure molecular distances.

The recent availability of green fluorescent protein (GFP) mutants with shifted excitation and emission spectra has made it feasible to measure protein-protein interactions by using GFP tags as intracellular markers. GFP-tagged protein chimeras are expressed intracellularly and do not require any chemical treatment to become fluorescent. FRET can also occur between fusions of blue-emitting and green-emitting GFP variants.

As described above, a donor fluorescent protein label is capable of absorbing a photon and transferring energy to another fluorescent label. The acceptor fluorescent protein label is capable of absorbing energy and emitting a photon. If needed, the linker connects the binding domain, sequence or polypeptide either directly, or indirectly through an intermediary linkage, with one or both of the donor and acceptor fluorescent protein labels or the fluorescent label and, optionally, the quencher if a non-FRET assay is being performed. Regardless of the relative order of the binding domain, sequence or polypeptide or its binding partner and the donor and acceptor fluorescent protein labels on a polypeptide molecule, it is essential that sufficient distance be placed between the donor and acceptor or the fluorescent label and corresponding quencher by the linker and/or the binding domain, sequence, nucleic acid or polypeptide and corresponding binding partner to ensure that FRET does not occur unless the binding domain, sequence or polypeptide and its binding partner bind. It is desirable, as described in greater detail in WO97/28261, to select a donor fluorescent protein label with an emission spectrum that overlaps with the excitation spectrum of an acceptor fluorescent protein label. In some embodiments of the invention the overlap in emission and excitation spectra will facilitate FRET. A fluorescent protein of use in the invention includes, in addition to those with intrinsic fluorescent properties, proteins that fluoresce due to intramolecular rearrangements or the addition of cofactors that promote fluorescence.

For example, green fluorescent proteins (GFPs) of cnidarians, which act as their energy-transfer acceptors in bioluminescence, can be used in the invention. A green fluorescent protein, as used herein, is a protein that fluoresces green light, and a blue fluorescent protein is a protein that fluoresces blue light. GFPs have been isolated from the Pacific Northwest jellyfish, *Aequorea victoria*, from the sea pansy, *Renilla reniformis*, and from *Phialidium gregarium* (Ward et al., 1982, *Photochem. Photobiol.* 35:803-808; Levine et al., 1982, *Comp. Biochem. Physiol.* 72B:77-85). A variety of *Aequorea*-related GFPs having useful excitation and emission spectra have been engineered by modifying the amino acid sequence of a naturally-occurring GFP from *Aequorea Victoria* (Prasher et al., 1992, *Gene* 111:229-233; Heim et al., 1994, *Proc. Natl. Acad. Sci. U.S.A.* 91:12501-12504; PCTUS95/ 14692). As used herein, a fluorescent protein is an *Aequorea*-related fluorescent protein if any contiguous sequence of 150 amino acids of the fluorescent protein has at least 85% sequence identity with an amino acid sequence, either contiguous or non-contiguous, from the wild-type *Aequorea* green fluorescent protein (SwissProt Accession No. P42212). Similarly, the fluorescent protein may be related to *Renilla* or *Phialidium* wild-type fluorescent proteins using the same standards. *Aequorea*-related fluorescent proteins include, for example, wild-type (native) *Aequorea victoria* GFP, whose nucleotide and deduced amino acid sequences are presented in GenBank Accession Nos. L29345, M62654, M62653 and other *Aequorea*-related engineered versions of Green Fluorescent Protein, of which some are listed above. Several of these, i.e., P4, P4-3, W7 and W2 fluoresce at a distinctly shorter wavelength than wild type.

Recombinant nucleic acid molecules encoding single- or tandem fluorescent protein/polypeptide comprising engineered binding domain, sequences or polypeptides or their binding partners useful in the invention may be expressed for in vivo assays of the activity of a modifying enzyme on the encoded products.

Similar assays using different ligands, different detection techniques, etc. are readily designed by one of skill in the art using the information provided in the art generally.

Vectors Useful for the Invention

There is a wide array of vectors known and available in the art that are useful for the expression of differentially expressed nucleic acid molecules according to the invention. The selection of a particular vector clearly depends upon the intended use the polypeptide encoded by the differentially expressed nucleic acid. For example, the selected vector must be capable of driving expression of the polypeptide in the desired cell type, whether that cell type be prokaryotic or eukaryotic. Many vectors comprise sequences allowing both prokaryotic vector replication and eukaryotic expression of operably linked gene sequences.

Vectors useful according to the invention may be autonomously replicating, that is, the vector, for example, a plasmid, exists extrachromosomally and its replication is not necessarily directly linked to the replication of the host cell's genome. Alternatively, the replication of the vector may be linked to the replication of the host's chromosomal DNA, for example, the vector may be integrated into the chromosome of the host cell as achieved by retroviral vectors.

Vectors useful according to the invention preferably comprise sequences operably linked to the differentially expressed sequences that permit the transcription and translation of the sequence. Sequences that permit the transcription of the linked differentially expressed sequence include a promoter and optionally also include an enhancer element or elements permitting the strong expression of the linked sequences. The term "transcriptional regulatory sequences" refers to the combination of a promoter and any additional sequences conferring desired expression characteristics (e.g., high level expression, inducible expression, tissue- or cell-type-specific expression) on an operably linked nucleic acid sequence.

The selected promoter may be any DNA sequence that exhibits transcriptional activity in the selected host cell, and may be derived from a gene normally expressed in the host cell or from a gene normally expressed in other cells or organisms. Examples of promoters include, but are not limited to the following: A) prokaryotic promoters—*E. coli* lac, tac, or trp promoters, lambda phage PR or PL promoters, bacteriophage T7, T3, Sp6 promoters, *B. subtilis* alkaline protease promoter, and the *B. stearothermophilus* maltogenic amylase promoter, etc.; B) eukaryotic promoters—yeast promoters, such as GAL1, GAL4 and other glycolytic gene promoters (see for example, Hitzeman et al., 1980, J. Biol. Chem. 255: 12073-12080; Alber & Kawasaki, 1982, J. Mol. Appl. Gen. 1: 419-434), LEU2 promoter (Martinez-Garcia et al., 1989, Mol Gen Genet. 217: 464-470), alcohol dehydrogenase gene promoters (Young et al., 1982, in Genetic Engineering of Microorganisms for Chemicals, Hollaender et al., eds., Plenum Press, NY), or the TPI1 promoter (U.S. Pat. No. 4,599,311); insect promoters, such as the polyhedrin promoter (U.S. Pat. No. 4,745,051; Vasuvedan et al., 1992, FEBS Lett. 311: 7-11), the P10 promoter (Vlak et al., 1988, J. Gen. Virol. 69: 765-776), the *Autographa californica* polyhedrosis virus basic protein promoter (EP 397485), the baculovirus immediate-early gene promoter gene 1 promoter (U.S. Pat. Nos. 5,155,037 and 5,162,222), the baculovirus 39K delayed-early gene promoter (also U.S. Pat. Nos. 5,155,037 and 5,162, 222) and the OpMNPV immediate early promoter 2; mammalian promoters—the SV40 promoter (Subramani et al., 1981, Mol. Cell. Biol. 1: 854-864), metallothionein promoter (MT-1; Palmiter et al., 1983, Science 222: 809-814), adenovirus 2 major late promoter (Yu et al., 1984, Nucl. Acids Res. 12: 9309-21), cytomegalovirus (CMV) or other viral promoter (Tong et al., 1998, Anticancer Res. 18: 719-725), or even the endogenous promoter of a gene of interest in a particular cell type.

A selected promoter may also be linked to sequences rendering it inducible or tissue-specific. For example, the addition of a tissue-specific enhancer element upstream of a selected promoter may render the promoter more active in a given tissue or cell type. Alternatively, or in addition, inducible expression may be achieved by linking the promoter to any of a number of sequence elements permitting induction by, for example, thermal changes (temperature sensitive), chemical treatment (for example, metal ion- or IPTG-inducible), or the addition of an antibiotic inducing agent (for example, tetracycline).

Regulatable expression is achieved using, for example, expression systems that are drug inducible (e.g., tetracycline, rapamycin or hormone-inducible). Drug-regulatable promoters that are particularly well suited for use in mammalian cells include the tetracycline regulatable promoters, and glucocorticoid steroid-, sex hormone steroid-, ecdysone-, lipopolysaccharide (LPS)- and isopropylthiogalactoside (IPTG)-regulatable promoters. A regulatable expression system for use in mammalian cells should ideally, but not necessarily, involve a transcriptional regulator that binds (or fails to bind) non-mammalian DNA motifs in response to a regulatory agent, and a regulatory sequence that is responsive only to this transcriptional regulator.

Tissue-specific promoters may also be used to advantage in differentially expressed sequence-encoding constructs of the invention. A wide variety of tissue-specific promoters is known. As used herein, the term "tissue-specific" means that a given promoter is transcriptionally active (i.e., directs the expression of linked sequences sufficient to permit detection of the polypeptide product of the promoter) in less than all cells or tissues of an organism. A tissue specific promoter is preferably active in only one cell type, but may, for example, be active in a particular class or lineage of cell types (e.g., hematopoietic cells). A tissue specific promoter useful according to the invention comprises those sequences necessary and sufficient for the expression of an operably linked nucleic acid sequence in a manner or pattern that is essentially the same as the manner or pattern of expression of the gene linked to that promoter in nature. The following is a non-exclusive list of tissue specific promoters and literature references containing the necessary sequences to achieve expression characteristic of those promoters in their respective tissues; the entire content of each of these literature references is incorporated herein by reference. Examples of tissue specific promoters useful in the present invention are as follows:

Bowman et al., 1995 Proc. Natl. Acad. Sci. USA 92, 12115-12119 describe a brain-specific transferrin promoter; the synapsin I promoter is neuron specific (Schoch et al., 1996 J.

Biol. Chem. 271, 3317-3323); the nestin promoter is postmitotic neuron specific (Uetsuki et al., 1996 J. Biol. Chem. 271, 918-924); the neurofilament light promoter is neuron specific (Charron et al., 1995 J. Biol. Chem. 270, 30604-30610); the acetylcholine receptor promoter is neuron specific (Wood et al., 1995 J. Biol. Chem. 270, 30933-30940); and the potassium channel promoter is high-frequency firing neuron specific (Gan et al., 1996 J. Biol. Chem 271, 5859-5865). Any tissue specific transcriptional regulatory sequence known in the art may be used to advantage with a vector encoding a differentially expressed nucleic acid sequence obtained from an animal subjected to pain.

In addition to promoter/enhancer elements, vectors useful according to the invention may further comprise a suitable terminator. Such terminators include, for example, the human growth hormone terminator (Palmiter et al., 1983, supra), or, for yeast or fungal hosts, the TPI1 (Alber & Kawasaki, 1982, supra) or ADH3 terminator (McKnight et al., 1985, EMBO J. 4: 2093-2099).

Vectors useful according to the invention may also comprise polyadenylation sequences (e.g., the SV40 or Ad5E1b poly(A) sequence), and translational enhancer sequences (e.g., those from Adenovirus VA RNAs). Further, a vector useful according to the invention may encode a signal sequence directing the recombinant polypeptide to a particular cellular compartment or, alternatively, may encode a signal directing secretion of the recombinant polypeptide.

a. Plasmid Vectors.

Any plasmid vector that allows expression of a differentially expressed coding sequence of the invention in a selected host cell type is acceptable for use according to the invention. A plasmid vector useful in the invention may have any or all of the above-noted characteristics of vectors useful according to the invention. Plasmid vectors useful according to the invention include, but are not limited to the following examples: Bacterial—pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223-3, pKK233-3, pDR540, and pRIT5 (Pharmacia); Eukaryotic—pWLneo, pSV2cat, pOG44, pXT1, pSG (Stratagene) pSVK3, pBPV, pMSG, and pSVL (Pharmacia). However, any other plasmid or vector may be used as long as it is replicable and viable in the host.

b. Bacteriophage Vectors.

There are a number of well known bacteriophage-derived vectors useful according to the invention. Foremost among these are the lambda-based vectors, such as Lambda Zap II or Lambda-Zap Express vectors (Stratagene) that allow inducible expression of the polypeptide encoded by the insert. Others include filamentous bacteriophage such as the M13-based family of vectors.

c. Viral Vectors.

A number of different viral vectors are useful according to the invention, and any viral vector that permits the introduction and expression of one or more of the differentially expressed polynucleotides of the invention in cells is acceptable for use in the methods of the invention. Viral vectors that can be used to deliver foreign nucleic acid into cells include but are not limited to retroviral vectors, adenoviral vectors, adeno-associated viral vectors, herpesviral vectors, and Semliki forest viral (alphaviral) vectors. Defective retroviruses are well characterized for use in gene transfer (for a review see Miller, A. D. (1990) Blood 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14, and other standard laboratory manuals.

In addition to retroviral vectors, Adenovirus can be manipulated such that it encodes and expresses a gene product of interest but is inactivated in terms of its ability to replicate in a normal lytic viral life cycle (see for example Berkner et al., 1988, BioTechniques 6:616; Rosenfeld et al., 1991, Science 252:431-434; and Rosenfeld et al., 1992, Cell 68:143-155). Suitable adenoviral vectors derived from the adenovirus strain Ad type 5 d1324 or other strains of adenovirus (e.g., Ad2, Ad3, Ad7 etc.) are well known to those skilled in the art. Adeno-associated virus (AAV) is a naturally occurring defective virus that requires another virus, such as an adenovirus or a herpes virus, as a helper virus for efficient replication and a productive life cycle. (For a review see Muzyczka et al., 1992, Curr. Topics in Micro. and Immunol. 158:97-129). An AAV vector such as that described in Traschin et al. (1985, Mol. Cell. Biol. 5:3251-3260) can be used to introduce nucleic acid into cells. A variety of nucleic acids have been introduced into different cell types using AAV vectors (see, for example, Hermonat et al., 1984, Proc. Natl. Acad. Sci. USA 81: 6466-6470; and Traschin et al., 1985, Mol. Cell. Biol. 4: 2072-2081).

Host Cells

Any cell into which a recombinant vector carrying a gene encoding a nucleic acid sequence differentially expressed in an animal subjected to pain may be introduced and wherein the vector is permitted to drive the expression of the peptide encoded by the differentially expressed sequence is useful according to the invention. Any cell in which a differentially expressed molecule of the invention may be expressed and preferably detected is a suitable host, wherein the host cell is preferably a mammalian cell and more preferably a human cell. Vectors suitable for the introduction of differentially expressed nucleic acid sequences to host cells from a variety of different organisms, both prokaryotic and eukaryotic, are described herein above or known to those skilled in the art.

Host cells may be prokaryotic, such as any of a number of bacterial strains, or may be eukaryotic, such as yeast or other fungal cells, insect or amphibian cells, or mammalian cells including, for example, rodent, simian or human cells. Cells may be primary cultured cells, for example, primary human fibroblasts or keratinocytes, or may be an established cell line, such as NIH3T3, 293T or CHO cells. Further, mammalian cells useful in the present invention may be phenotypically normal or oncogenically transformed. It is assumed that one skilled in the art can readily establish and maintain a chosen host cell type in culture.

Introduction of Vectors to Host Cells.

Vectors useful in the present invention may be introduced to selected host cells by any of a number of suitable methods known to those skilled in the art. For example, vector constructs may be introduced to appropriate bacterial cells by infection, in the case of E. coli bacteriophage vector particles such as lambda or M13, or by any of a number of transformation methods for plasmid vectors or for bacteriophage DNA. For example, standard calcium-chloride-mediated bacterial transformation is still commonly used to introduce naked DNA to bacteria (Sambrook et al., 1989, Molecular Cloning, A Laboratory Manual, Cold Spring Harbor Laboratory Press, Cold Spring Harbor, N.Y.), but electroporation may also be used (Ausubel et al., 1988, Current Protocols in Molecular Biology, (John Wiley & Sons, Inc., NY, N.Y.)).

For the introduction of vector constructs to yeast or other fungal cells, chemical transformation methods are generally used (e.g. as described by Rose et al., 1990, Methods in Yeast Genetics, Cold Spring Harbor Laboratory Press, Cold Spring Harbor, N.Y.). For transformation of *S. cerevisiae*, for example, the cells are treated with lithium acetate to achieve transformation efficiencies of approximately 104 colony-forming units (transformed cells)/µg of DNA. Transformed cells are then isolated on selective media appropriate to the selectable marker used. Alternatively, or in addition, plates or filters lifted from plates may be scanned for GFP fluorescence to identify transformed clones.

For the introduction of vectors comprising differentially expressed sequences to mammalian cells, the method used will depend upon the form of the vector. Plasmid vectors may be introduced by any of a number of transfection methods, including, for example, lipid-mediated transfection ("lipofection"), DEAE-dextran-mediated transfection, electroporation or calcium phosphate precipitation. These methods are detailed, for example, in Current Protocols in Molecular Biology (Ausubel et al., 1988, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. For example, Lipofectamine™ (Life Technologies) or Lipo-Taxi™ (Stratagene) kits are available. Other companies offering reagents and methods for lipofection include BioRad Laboratories, CLONTECH, Glen Research, InVitrogen, JBL Scientific, MBI Fermentas, PanVera, Promega, Quantum Biotechnologies, Sigma-Aldrich, and Wako Chemicals USA.

Following transfection with a vector of the invention, eukaryotic (e.g., human) cells successfully incorporating the construct (intra- or extrachromosomally) may be selected, as noted above, by either treatment of the transfected population with a selection agent, such as an antibiotic whose resistance gene is encoded by the vector, or by direct screening using, for example, FACS of the cell population or fluorescence scanning of adherent cultures. Frequently, both types of screening may be used, wherein a negative selection is used to enrich for cells taking up the construct and FACS or fluorescence scanning is used to further enrich for cells expressing differentially expressed polynucleotides or to identify specific clones of cells, respectively. For example, a negative selection with the neomycin analog G418 (Life Technologies, Inc.) may be used to identify cells that have received the vector, and fluorescence scanning may be used to identify those cells or clones of cells that express the vector construct to the greatest extent.

Test Compounds According to the Invention

Whether in vitro or in an in vivo system, the invention encompasses methods by which to screen compositions which may enhance or inhibit the formation of FANCD2-containing foci. Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds are readily modified through conventional chemical, physical, and biochemical means.

Useful compounds may be found within numerous chemical classes, though typically they are organic compounds, including small organic compounds. Small organic compounds have a molecular weight of more than 50 yet less than about 2,500 Daltons, preferably less than about 750, more preferably less than about 350 Daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g., for the amino group, acylation or alkylation, and for the carboxyl group, esterification or amidification, or the like.

Candidate modulators which may be screened according to the methods of the invention include receptors, enzymes, ligands, regulatory factors, and structural proteins. Candidate modulators also include nuclear proteins, cytoplasmic proteins, mitochondrial proteins, secreted proteins, plasmalemma-associated proteins, serum proteins, viral antigens, bacterial antigens, protozoan antigens and parasitic antigens. Candidate modulators additionally comprise proteins, lipoproteins, glycoproteins, phosphoproteins and nucleic acids (e.g., RNAs such as ribozymes or antisense nucleic acids). Proteins or polypeptides which can be screened using the methods of the present invention include hormones, growth factors, neurotransmitters, enzymes, clotting factors, apolipoproteins, receptors, drugs, oncogenes, tumor antigens, tumor suppressors, structural proteins, viral antigens, parasitic antigens, bacterial antigens and antibodies (see below).

Candidate modulators which may be screened according to the invention also include substances for which a test cell or organism might be deficient or that might be clinically effective in higher-than-normal concentration as well as those that are designed to eliminate the translation of unwanted proteins. Nucleic acids of use according to the invention not only may encode the candidate modulators described above, but may eliminate or encode products which eliminate deleterious proteins. Such nucleic acid sequences are antisense RNA and ribozymes, as well as DNA expression constructs that encode them. Note that antisense RNA molecules, ribozymes or genes encoding them may be administered to a test cell or organism by a method of nucleic acid delivery that is known in the art, as described below. Inactivating nucleic acid sequences may encode a ribozyme or antisense RNA specific for the target mRNA. Ribozymes of the hammerhead class are the smallest known, and lend themselves both to in vitro production and delivery to cells (summarized by Sullivan, 1994, J. Invest. Dermatol., 103: 85S-98S; Usman et al., 1996, Curr. Opin. Struct. Biol., 6: 527-533).

Therapeutic Compositions According to the Invention

Modulators of FANCD2-containing foci formation may be useful therapeutic agents. For example, enhancers of FANCD2-containing foci formation, whether in the presence or absence of genotoxic agents, may be useful for providing protection of a subject against genotoxic agents. If a compound which has been identified in a screen of the present invention or through other means to enhance formation of FANCD2-containing foci and is not itself a genotoxic agent, then such a compound may be a useful as a protective agent. Desferrioxamine (DFO) [1-Amino-6,17-dihydroxy-7,10,18,21-tetraoxo-27-(n-acetylhydroxylamino)-6,11,17,22-tetraazaheptaeicosane; CAS Registry No: 70-51-9] was identified as an agonist of the FA/BRCA pathway. DFO is a potent activator of FANCD2 monoubiquitination and foci assembly. DFO is a known chelator of iron, and it is believed to decrease intracellular oxygen radicals (Breuer et al., (2001) Blood, 97, 792-798). The identification of DFO as an agonist of the FA/BRCA pathway has important implications. Although DFO is a safe drug, in clinical use, it may also serve to prime the FA/BRCA DNA repair pathway. As such, it could be a useful and safe protective agent against genotoxic agents. At present there are few known protective agents. For instance, amifostine is approved for radiation protection (Choi, (2003) Semin Oncol. 30, 10-17). Thus a therapeutic amount DFO could be administered to a subject in order to provide protection of the subject from genotoxic agents. There are many obvious uses of such an agent which enhances FANCD2-containing foci formation without itself having genotoxic effects, such as during radiation exposure in warfare, following a radioactive spill, or during space travel to Mars.

Likewise, a modulator which reduces the formation of FANCD2-containing foci may have many uses. An obvious use of an agent which inhibits the FA/BRCA DNA repair pathway would be for its use as a chemosensitizer during chemotherapy. It is known in the art that any tumors develop resistance to chemotherapy. A combination therapy comprising an anticancer therapeutic agent and a chemosensitizer may greatly reduce the resistance of these tumors towards the anticancer agent. Even in cases where resistance is not shown to be a problem, it may be advantageous to administer such a combination therapy if the administered dose of the anticancer agent can be reduced or if such a treatment diminishes the overall side effects of the anticancer agent. Using the screening methods described in the present invention, Wortmannin and Trichostatin A were identified as inhibitors of the FANCD2-containing foci formation. These compounds, therefore, may be useful as chemosensitizers.

Pharmaceutical Compositions Comprising Modulators of FANCD2-Containing foci Formation In another embodiment, the invention relates to a pharmaceutical composition comprising a, as described in the preceding section, and a pharmaceutically acceptable carrier, as described below. The pharmaceutical composition comprising the modulator of FANCD2-containing foci formation is useful for treating a variety of diseases and disorders including cancer, and may be useful as protective agents against genotoxic agents.

The compounds of the present invention, or pharmaceutically acceptable salts thereof, can be formulated for oral, intravenous, intramuscular, subcutaneous, topical or parenteral administration for the therapeutic or prophylactic treatment of diseases. For oral or parental administration, compounds of the present invention can be mixed with conventional pharmaceutical carriers and excipients and used in the form of tablets, capsules, elixirs, suspensions, syrups, wafers and the like. The compositions comprising a compound of this present invention will contain from about 0.1% to about 99.9%, about 1% to about 98%, about 5% to about 95%, about 10% to about 80% or about 15% to about 60% by weight of the active compound.

The pharmaceutical preparations disclosed herein are prepared in accordance with standard procedures and are administered at dosages that are selected to reduce, prevent, or eliminate cancer, or to provide a protective effect against genotoxic agents such as ionizing radiation. (See, e.g., *Remington's Pharmaceutical Sciences*, Mack Publishing Company, Easton, Pa.; and Goodman and Gilman, *Pharmaceutical Basis of Therapeutics*, Pergamon Press, New York, N.Y., the contents of which are incorporated herein by reference, for a general description of the methods for administering various antimicrobial agents for human therapy). The compositions of the present invention can be delivered using controlled (e.g., capsules) or sustained release delivery systems (e.g., bioerodable matrices). Exemplary delayed release delivery systems for drug delivery that are suitable for administration of the compositions of the invention are described in U.S. Pat. No. 4,452,775 (issued to Kent), U.S. Pat. No. 5,239,660 (issued to Leonard), U.S. Pat. No. 3,854,480 (issued to Zaffaroni).

The pharmaceutically acceptable compositions of the present invention comprise one or more compounds of the present invention in association with one or more non-toxic, pharmaceutically acceptable carriers and/or diluents and/or adjuvants and/or excipients, collectively referred to herein as "carrier" materials, and if desired other active ingredients. The compositions may contain common carriers and excipients, such as corn starch or gelatin, lactose, sucrose, microcrystalline cellulose, kaolin, mannitol, dicalcium phosphate, sodium chloride and alginic acid. The compositions may contain crosarmellose sodium, microcrystalline cellulose, sodium starch glycolate and alginic acid.

Tablet binders that can be included are acacia, methylcellulose, sodium carboxymethylcellulose, polyvinylpyrrolidone (Providone), hydroxypropyl methylcellulose, sucrose, starch and ethylcellulose.

Lubricants that can be used include magnesium stearate or other metallic stearates, stearic acid, silicon fluid, talc, waxes, oils and colloidal silica.

Flavoring agents such as peppermint, oil of wintergreen, cherry flavoring or the like can also be used. It may also be desirable to add a coloring agent to make the dosage form more aesthetic in appearance or to help identify the product comprising a compound of the present invention.

For oral use, solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica or talc: disintegrants, for example, potato starch, flavoring or coloring agents, or acceptable wetting agents. Oral liquid preparations generally are in the form of aqueous or oily solutions, suspensions, emulsions, syrups or elixirs and may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl parahydroxybenzoate, propylene glycol, sorbitol, or sorbic acid.

For intravenous (iv) use, compounds of the present invention can be dissolved or suspended in any of the commonly used intravenous fluids and administered by infusion. Intravenous fluids include, without limitation, physiological saline or Ringer's solution.

Formulations for parental administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For intramuscular preparations, a sterile formulation of compounds of the present invention or suitable soluble salts forming the compound, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g. an ester of a long chain fatty acid such as ethyl oleate.

For topical use the compounds of present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compound of the present invention can be in powder form for reconstitution in the appropriate pharmaceutically acceptable carrier at the time of delivery. In another embodiment, the unit dosage form of the compound can be a solution of the compound or a salt thereof in a suitable diluent in sterile, hermetically sealed ampoules.

The amount of the compound of the present invention in a unit dosage comprises a therapeutically-effective amount of at least one active compound of the present invention which may vary depending on the recipient subject, route and frequency of administration. A recipient subject refers to a plant, a cell culture or an animal such as an ovine or a mammal including a human.

According to this aspect of the present invention, the novel compositions disclosed herein are placed in a pharmaceutically acceptable carrier and are delivered to a recipient subject (including a human subject) in accordance with known methods of drug delivery. In general, the methods of the invention for delivering the compositions of the invention in vivo utilize art-recognized protocols for delivering the agent with the only substantial procedural modification being the substitution of the compounds of the present invention for the drugs in the art-recognized protocols.

The compounds of the present invention provide a method for treating pre-cancerous or cancerous conditions, or for use as a protective agent against genotoxic agents. As used herein, the term "unit dosage" refers to a quantity of a therapeutically effective amount of a compound of the present invention that elicits a desired therapeutic response. The term "treating" is defined as administering, to a subject, a therapeutically effective amount of at least one compound of the present invention, both to prevent the occurrence of a pre-cancer or cancer condition, or to control or eliminate pre-cancer or cancer condition. The term "desired therapeutic response" refers to treating a recipient subject with a compound of the present invention such that a pre-cancer or cancer condition is reversed, arrested or prevented in a recipient subject.

The compounds of the present invention can be administered as a single daily dose or in multiple doses per day. The treatment regime may require administration over extended periods of time, e.g., for several days or for from two to four weeks. The amount per administered dose or the total amount administered will depend on such factors as the nature and severity of the disease condition, the age and general health of the recipient subject, the tolerance of the recipient subject to the compound and the type of cancer, the sensitivity of the cancer to therapeutic agents, and, if used in combination with other therapeutic agent(s), the dose and type of therapeutic agent(s) used.

A compound according to this invention may also be administered in the diet or feed of a patient or animal. The diet for animals can be normal foodstuffs to which the compound can be added or it can be added to a premix.

The compounds of the present invention may be taken in combination, together or separately with any known clinically approved agent to treat a recipient subject in need of such treatment.

Kits According to the Invention

For convenience, the conventional reagents for immunohistochemical analysis or immunofluorescent microscopy, or other diagnostic assays according to this invention are provided in the form of kits. Such kits are useful for determining and enumerating the absence or presence of FANCD2-containing foci in samples from a living subject. Thus, such a kit will be useful in conducting the diagnostic assays in determining if a subject has recently been exposed to a genotoxic agent, the degree of exposure of the subject to a genotoxic agent, and the sensitivity of a subject to genotoxic agents. Such a diagnostic kit comprises a FANCD2 ligand (e.g., an antibody capable of binding to FANCD2) or a monoubiquitinated FANCD2 ligand of this invention. The kits may also include instructions for performing the assay, microscopic slides for fixing the tissue or cells, fixatives, suitable stains, various diluents and buffers, labeled conjugates for the detection of specifically bound compositions and other signal-generating reagents, such as fluorescent compounds and dyes, enzyme substrates, cofactors and chromogens. Additional components may include indicator charts for fluorescent or colorimetric comparisons, disposable gloves, decontamination instructions, applicator sticks or containers, and a sample preparator cup. Such kits provide a convenient, efficient way for a clinical laboratory to diagnose the presence or absence of DNA damage in a cell or tissue according to this invention. Kits according to the invention include appropriate packaging means, for example test tubes, tissue culture plates and multiwell plates. Ligands can be provided in a solution or in a lyophilized form.

The present invention is described by reference to the following Examples, which are offered by way of illustration and are not intended to limit the invention in any manner. Standard techniques well known in the art or the techniques specifically described below were utilized. All references cited herein are incorporated by reference.

EXAMPLES

Example 1

Development of an Antibody that Specifically Recognizes the Monoubiquitinated Isoform of FANCD2

Figure 10:
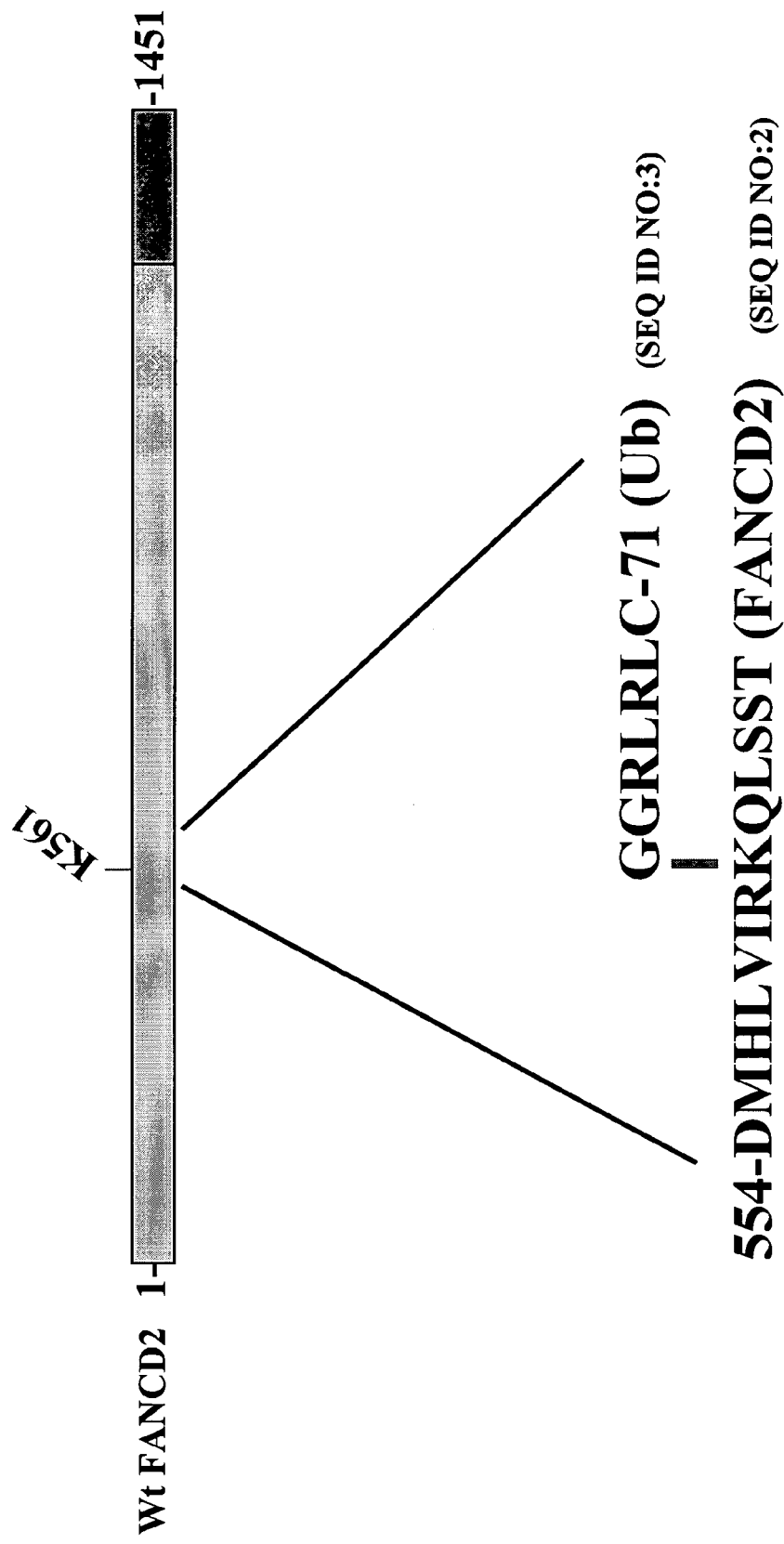
FIG. 10. Generation of a monoclonal antibody specific for the monoubiquitinated (activated) isoform of FANCD2. A thirteen amino acid peptide, corresponding to an internal region of human FANCD2 (amino acids 554-566) was generated. This peptide contains lysine 561, the site of monoubiquitination. Via a gamma peptide linkage, we coupled a seven amino acid peptide (GGRLRLC) (SEQ ID NO:3), corresponding to the carboxyl terminus of ubiquitin to K561. This antigen was then coupled to KLH and used to immunize mice. Mice which developed a serologic response to the coupled antigen were sacrificed, and splenocyte fusion, for monoclonal antibody production, were performed.
Figure 11:
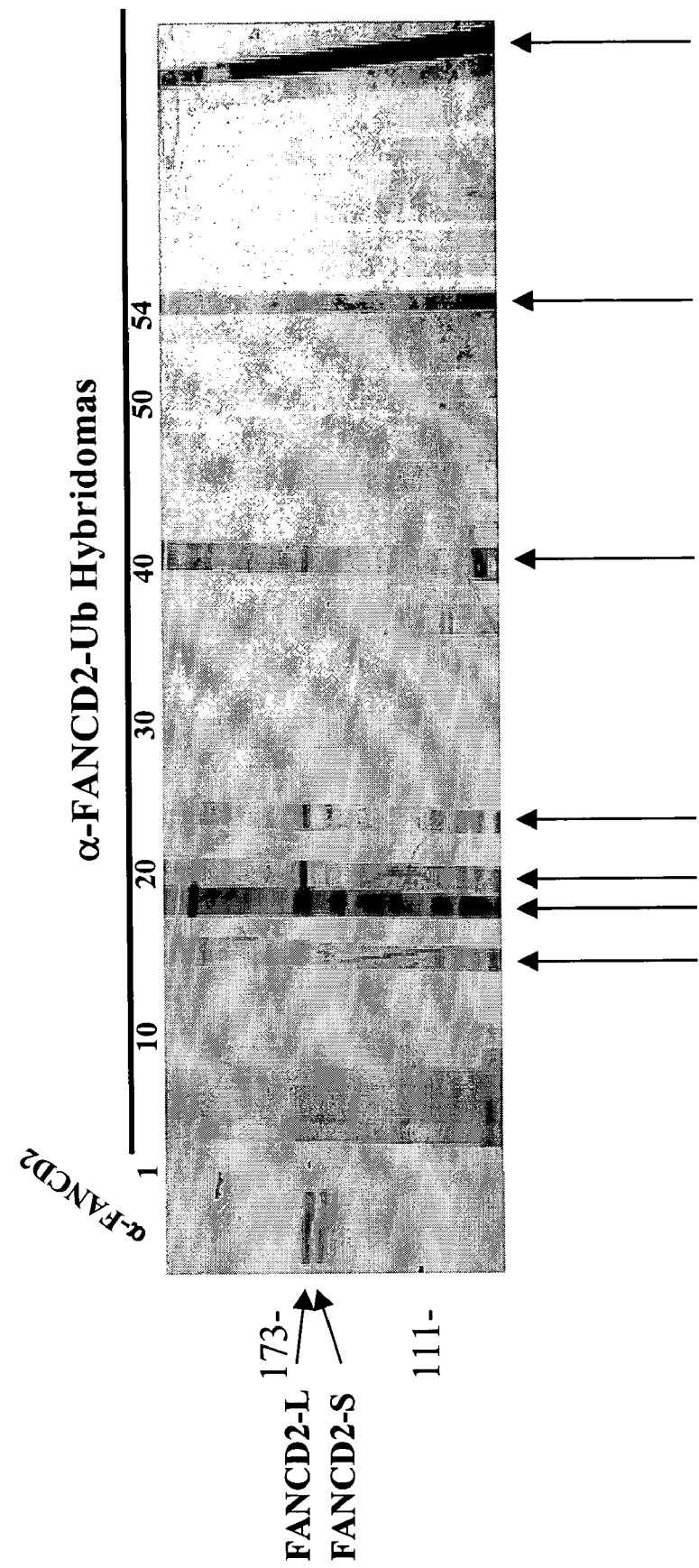
FIG. 11. Generation of hybridomas expressing monoclonal antibodies, specific for monoubiquitinated FANCD2. Following splenocyte fusion, murine hybridomas were subcloned, and supernatants were analyzed for their ability to recognize monoubiquitinated FANCD2 by western blot analysis. Six hybridomas were identified which specifically recognized monoubiquitinated FANCD2 by immunoblot, but did not recognize unmodified FANCD2. An antibody to monoubiquitinated FANCD2 provides a rapid FACS (fluorescent activated cell sorter) screen for peripheral blood lymphocytes (PBLs) which have been activated by radiation exposure.

Antibodies to FANCD2 (monoclonal and polyclonal) were raised against the amino terminal region of FANCD2. These antibodies recognize both isoforms of FANCD2 (FANCD2-S and FANCD2-L). To make an anti-FANCD2-L antibody, we have generated a specific antigen (FIG. 10), containing a region of FANCD2 linked covalently to the carboxyl terminus of ubiquitin (Ub). We injected mice with this antigen, and raised monoclonal antibodies (FIG. 11). These monoclonal antibodies will now be analyzed for their specific diagnostic value, as described above.

Example 2

Clinical Protocol for Taking Samples

Blood is drawn 24 to 48 hours after the alleged exposure, since, based on in vitro data, this is the peak time of foci formation. Again, different antisera, (say for FANCD2, BRCA1, and Histone 2AX) may differ significantly in the actual time of peak foci and in the duration of foci in vivo. Peripheral blood lymphocytes (PBLs) are isolated using a standard ficoll gradient. Cells are then stained with specific antisera to Histone 2AX, BRCA1, and FANCD2, and the percentage of cells with IRIFs and the number of IRIFs per cell are measured. Using a standard curve based on the amount of time which has elapsed since alleged radiation exposure, the likely dose of exposure to genotoxic agents is determined. Based on this dose, genotoxic protective agents are administered if needed.

I. Clinical Protocol

Oncology patients are enrolled who are receiving radiation or genotoxic chemotherapeutic agents for their tumor (head and neck squamous cell carcinoma patients, for example). Following radiation exposure, peripheral blood samples are drawn at different times after exposure (i.e., 1 hour, 3 hours, 8 hours, and 24 hours post exposure) and the number of foci in the peripheral blood lymphocytes are measured. In the case of samples from patients receiving radiation treatment, while the radiation field will only include the tumor region, blood (and lymphocytes) passing through this field will also receive a radiation exposure. Thus, a peripheral blood sample obtained from the patient will sample at least a fraction of the circulating lymphocytes which were irradiated in this field. A standard curve is generated correlating exposure (y-axis) with number of foci x-axis). Subsequently, a high throughput, automated instrument for measuring the radiation exposure of many individual blood samples is developed. This instrument is anticipated to work in the same principle as that used in previous assays to determine the exposure of a biological sample to radiation or genotoxic agent, in that it comprises contacting the biological sample with antibodies against proteins found in foci (FANCD2, Histone 2AX, BRCA1) and examining samples for foci formation using high-throughput automated microscopy.

Example 3

Dose-Dependent Generation of FANCD2 Monoubiquitination

Figure 12:
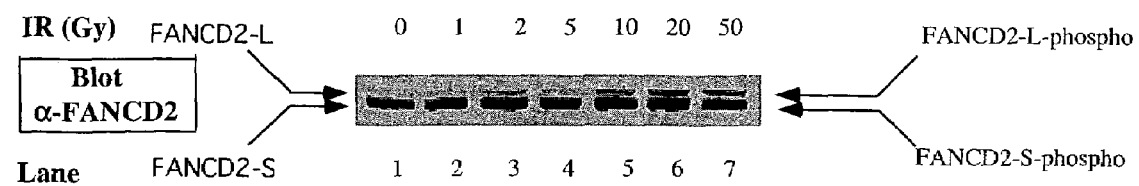
FIG. 12. Dose-dependent Generation of FANCD2 Monoubiquitination after IR. Exponentially growing HeLa cells were either untreated or exposed to the indicated IR dose. After four hours, cells were processed by anti-FANCD2 western blotting. Note that some activation of FANCD2 monoubiquitination can be observed in the low IR dose range (0-5 Gy radiation range).
Figure 13:
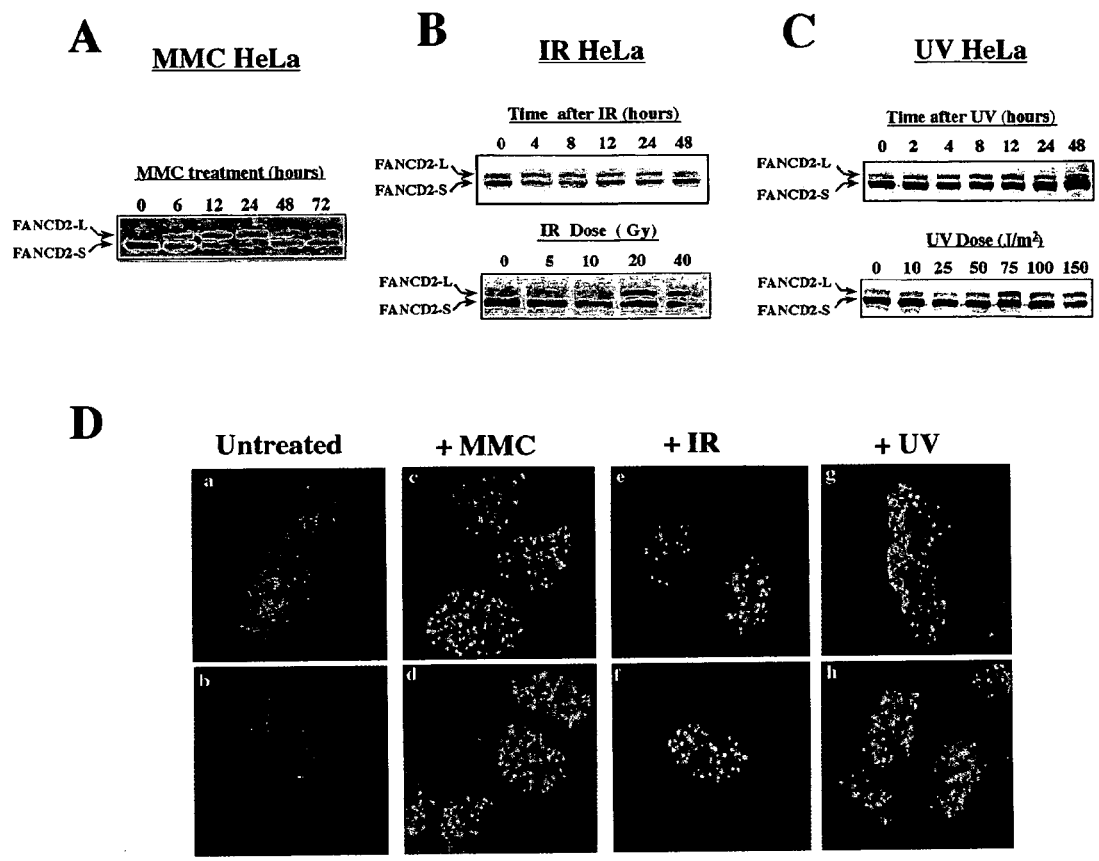
FIG. 13. Dose-dependent and Time-Course Dependent Generation of FANCD2 Monoubiquitination and FANCD2 Foci formation after Genotoxic Stress. Exponentially growing HeLa cells were either untreated or exposed to the indicated genotoxic agents (Mitomycin C, gamma irradiation, or ultraviolet light) and processed by western blotting (panels A, B, C) or immunofluorescence (panel D) with the polyclonal anti-FANCD2 antibody (E35).

We have previously shown that DNA damage activates FANCD2 monoubiquitination and that FANCD2 monoubiquitination correlates with FANCD2 nuclear foci formation (Garcia-Higuera et al., Mol Cell 7:249-262, 2001). As shown in FIG. 13, several kinds of genotoxic stresses (MMC, IR, ultraviolet light) can activate FANCD2 monoubiquitination (panel A, B, C) or FANCD2 foci formation (panel D). Interestingly, there was a time-course dependent and dose-dependent activation of FANCD2. In this analysis, FANCD2 foci were observed only 4 hours after IR and were observed after 5 Gy of IR (panel D). More refined studies (FIG. 12), also performed in HeLa cells, indicate a dose-dependent increase in FANCD2 monoubiquitination, even in the 0-5 Gy radiation range (i.e., low radiation exposure), further suggesting that FANCD2 foci formation may be a very sensitive indicator of radiation exposure. Preliminary studies indicate that irradiation of primary peripheral blood lymphocytes from normal adult human controls, in vitro, results in similar time-course and dose-dependent generation of FANCD2 nuclear foci (data not shown).

Example 4

Screening (Prescreen Using Chemicals)

I) High throughout Assay for an Inhibitor (or Agonist) of the Fanconi Anemia/BRCA Pathway.

An assay has been developed for the assembly of FANCD2 foci, a critical downstream event in the FA/BRCA pathway. For this purpose a fusion cDNA (FIG. 1) which encodes the GFP (green fluorescence protein), fused at the amino terminus of the full length FANCD2 protein, has been generated.

Figure 2:
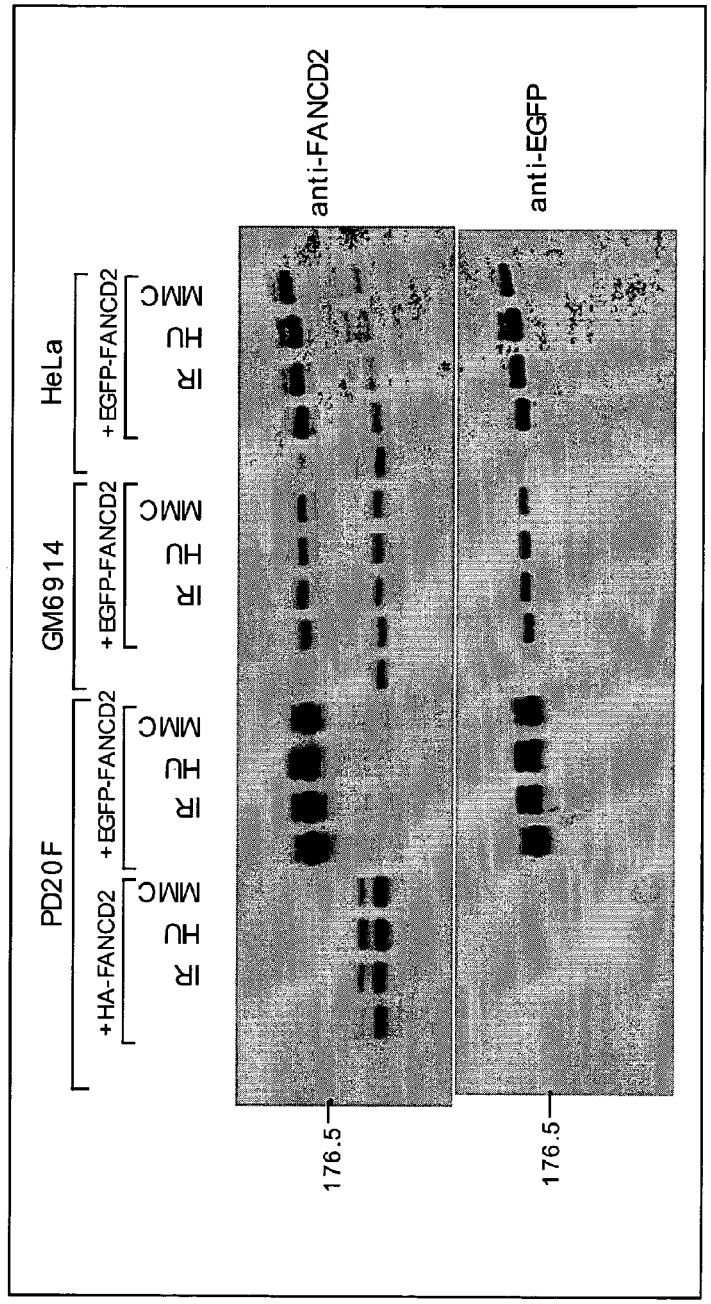
FIG. 2. The GFP-FANCD2 fusion protein is expressed and activated by monoubiquitination in transfected FA-D2 human fibroblasts. FANCD2-deficient human fibroblasts (PD20F) were either untransfected (lane 1), transfected with wild-type FANCD2 cDNA (lane 2-5), or transfected with the cDNA encoding the GFP-FANCD2 fusion protein (lane 6-9), as indicated. Alternatively, FA-A fibroblasts (GM6914, lanes 11-14) or HeLa cells (lanes 16-19) were transfected with the cDNA encoding the fusion protein. Cells were either untreated or exposed to genotoxic stress (ionizing radiation), as indicated. Whole cell lysates were analyzed by SDS-PAGE, and cellular proteins were immunoblotted with antisera to FANCD2. Conclusion: DNA damage activates the increased monoubiquitination of either the full-length (wild-type) FANCD2 protein or the GFP-FANCD2 fusion protein in corrected cells but not in FA cells.

Initially, this cDNA was transfected into PD20 (FA-D2 fibroblasts), which express no endogenous FANCD2 protein (FIG. 2) The GFP-FANCD2 protein is larger than FANCD2 (as predicted) and undergoes DNA damage-inducible monoubiquitination (lanes 6-9). When the GFP-FANCD2 protein was expressed in an FA-A (Fanconi Anemia subtype A) Fibroblast line, it was not monoubiquitinated, even when the cells were exposed to Ionizing Radiation (FIG. 2, lanes 11-14). Taken together, these results indicate that GFP-FANCD2 behaves similarly to the wild-type (untagged) FANCD2 protein.

Figure 3:
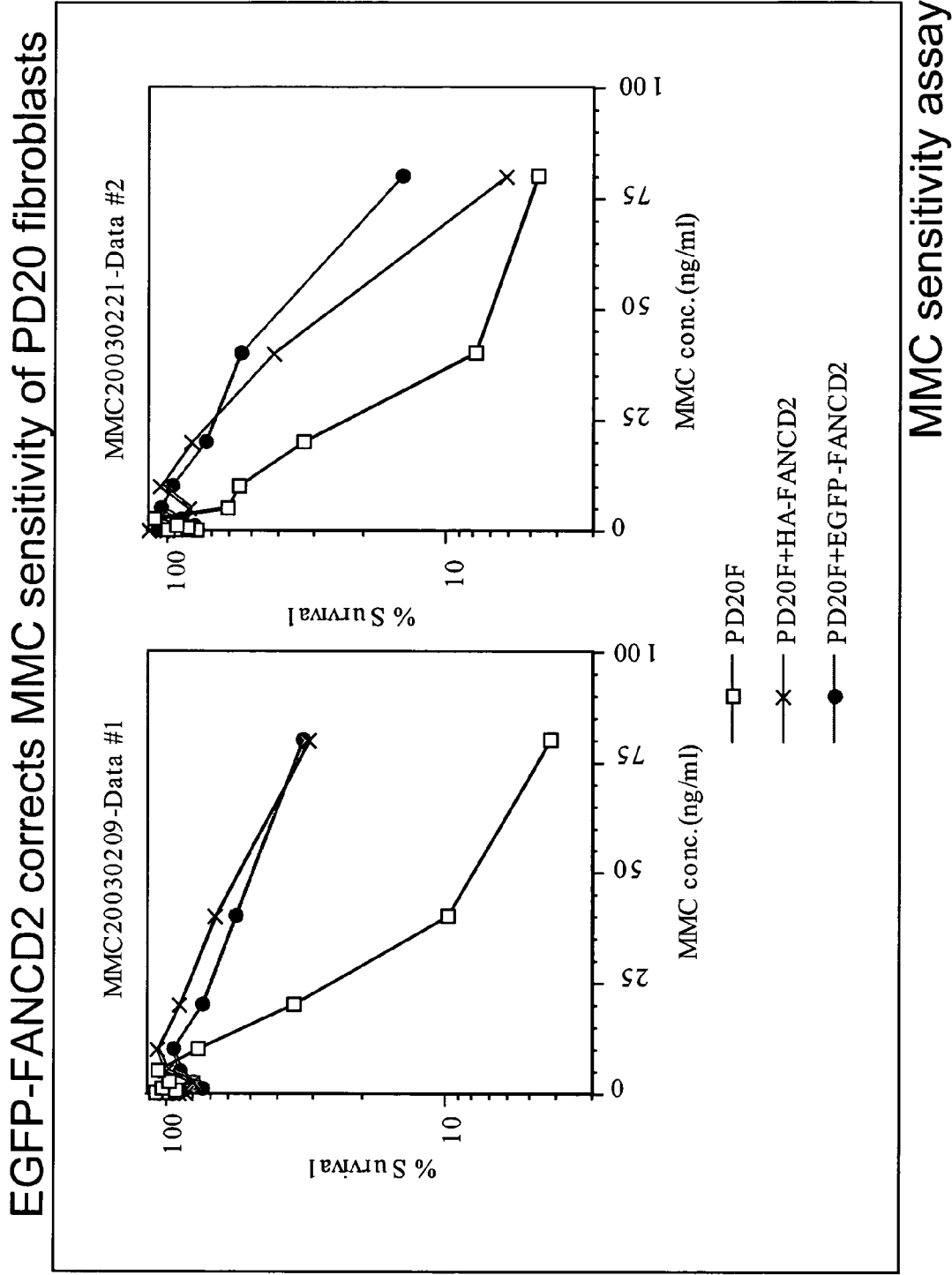
FIG. 3. The GFP-FANCD2 fusion protein functionally complements the Mitomycin C hypersensitivity of FANCD2-deficient human fibroblasts. The transfected PD20F cells, stably expressing GFP-FANCD2 protein, were analyzed for survival in variable concentrations of MMC. Conclusion: GFP-FANCD2 is functional, and it corrects the MMC hypersensitivity of PD20F cells. The GFP moiety at the amino terminus therefore does not interfere with its function in the cell.

Next it was determined whether GFP-FANCD2 can correct the MMC hypersensitivity of PD2OF cells (FIG. 3). Indeed, expression of GFP-FANCD2, like wild-type FANCD2, restores normal MMC resistance.

The PD2OF cells, expressing GFP-FANCD2 were plated and individual subclones isolated. One subclone (clone 7) expressed GFP-FANCD2 protein diffusely in its nucleus (FIG. 4). Following cellular exposure to IR, those cells formed bright, green foci in the nucleus. Thus, these cells are an ideal tool for high-throughput screening of antagonists and agonists of the FA/BRCA pathway.

II. Use of GFP-FANCD2 Expressing Fibroblasts to Identify Bioactive Small Molecule Regulators of the FA/BRCA Pathway.

Figure 5:
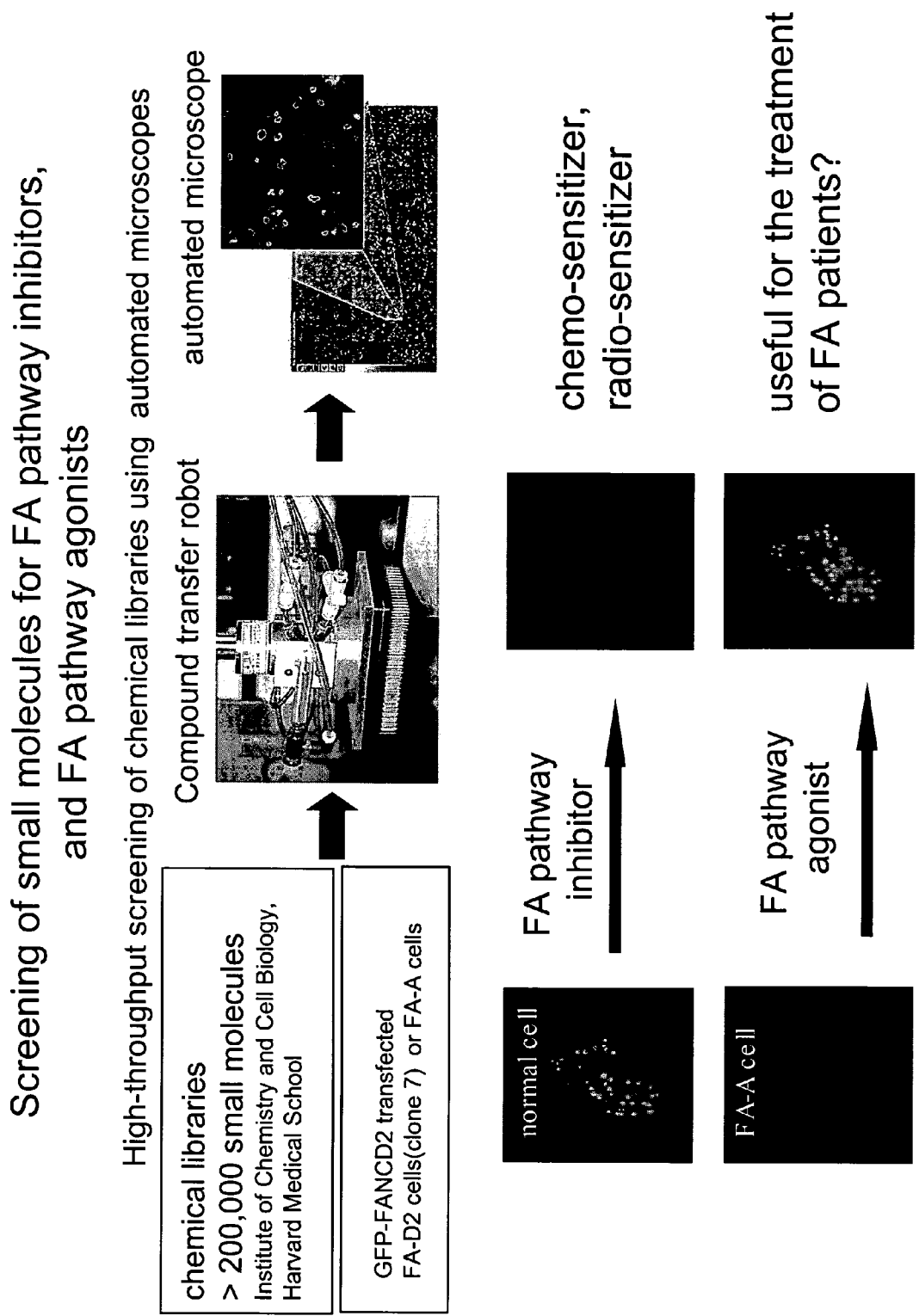
FIG. 5. A general method for screening for inhibitors and agonists of the Fanconi Anemia/BRCA pathway. Human fibroblasts (clone 7), stably expressing GFP-FANCD2, are exposed, in 384 well plates, to potential small molecule inhibitors or agonists compounds. Following pretreatment with these compounds, the plates are irradiated, to activate the monoubiquitination and foci formation of GFP-FANCD2. GFP-FANCD2 fails to form IR-inducible foci when expressed stably in a FA-A fibroblast. A small molecule agonist, which bypasses the FA enzyme complex, activates the foci formation in FA cells. Such a drug may be a suitable treatment for FA. Therefore, the GFP-FANCD2 fusion protein is used to screen either for inhibitors or agonists of the pathway.

A screening test was established in a core facility at Harvard Medical School called the ICCB (Institute for Chemistry and Chemical Biology). The general principle of this screening assay is shown in FIG. 5.

A small molecule transfer robot delivers chemical compounds to clone 7 fibroblasts, plated in 384-cell tissue culture plates. Several commercial libraries are available, comprising over 200,000 small molecules. Inhibitors of the FA/BRCA pathway are expected to block GFP-FANCD2 foci formation; agonists of the pathway will promote foci formation.

Figure 6:
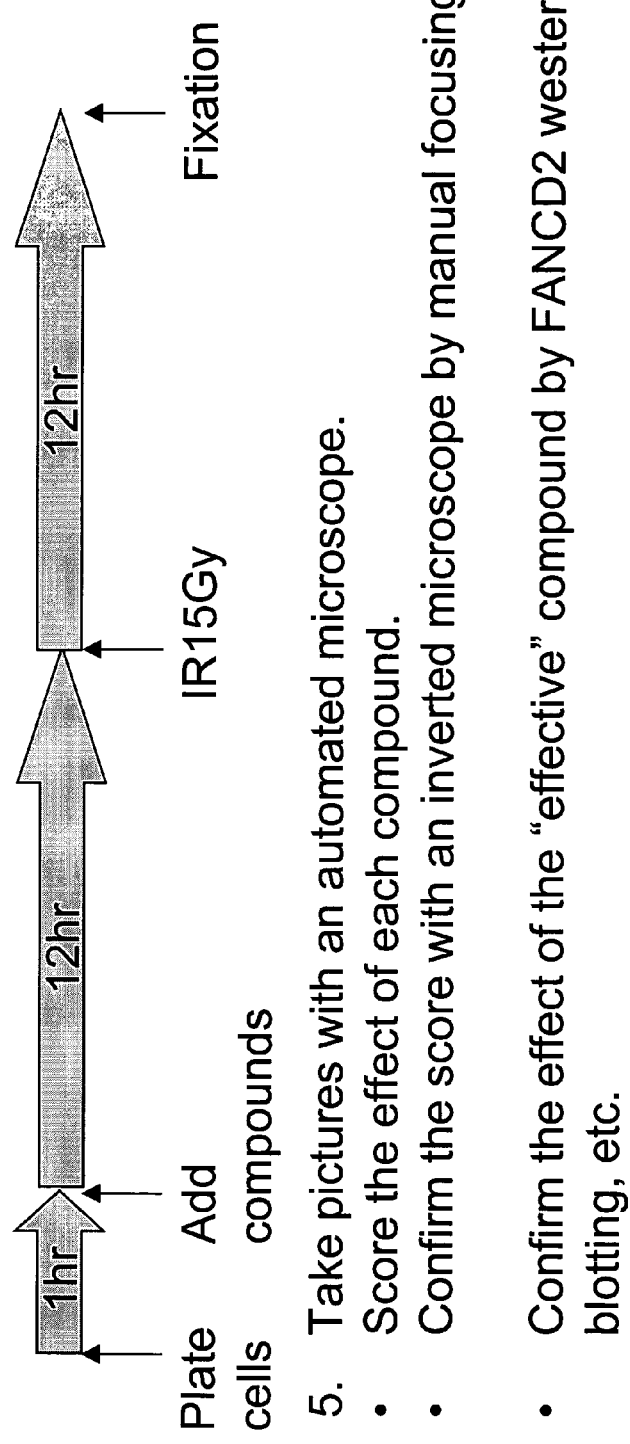
FIG. 6. Schematic protocol for the identification of small molecule inhibitors and agonists of the FA/BRCA pathway. Human fibroblasts, stably expressing GFP-FANCD2, are plated in 384-well plates, pretreated with chemical libraries, and exposed to Ionizing Radiation. GFP foci are scored, leading to the identification of inhibitors or agonists of the pathway.

The specific details of the assay are described in FIG. 6. As shown, the plated cells are preincubated with compounds (approximately 40 micromolar concentrations for twelve hours) before the stimulation with Ionizing Radiation. An important feature of the protocol is the use of secondary screens (FIG. 6, Point #8). Any compound initially found to inhibit or activate (i.e., synergize with) FANCD2 foci formation is subsequently screened in lower dose ranges (1-20 micromolar range) and is screened by two assays: (1) formation of FANCD2 foci and (2) activation of FANCD2 monoubiquitination (Western blot screen). Any compound which passes this secondary screen will then be examined for its ability to chemosensitize HeLa cells to the cytotoxic effects of cisplatin. (Taniguchi et al., (2003) Nat. Med 9:568-574).

III. Identification of Specific Compounds which Inhibit or Activate the FANCD2 Pathway.

Figure 7:
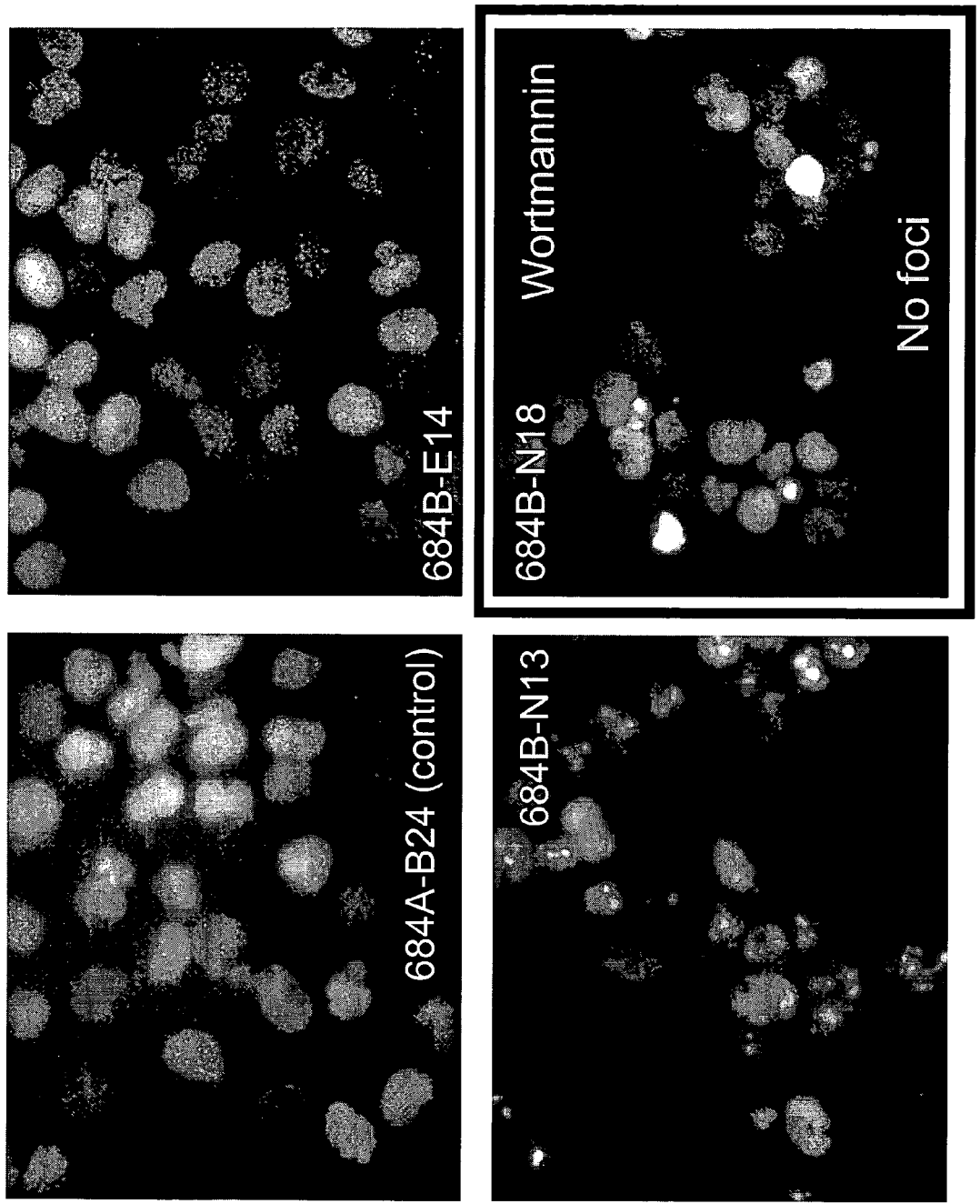
FIG. 7. Identification of Wortmannin and Trichostatin-A as inhibitors of the FA/BRCA pathway. Using the strategy outlined in FIG. 6, a chemical library, containing over 1000 independent compounds was screened. Most compounds had no effect on the formation of IR-inducible GFP-FANCD2 foci. Two compounds (Trichostatin A, a known HDAC inhibitor and wortmannin, a known ATR-kinase inhibitor) efficiently blocked foci formation. Taken together, these results suggest that cellular HDAC activity (i.e., histone deacetylase activity) and ATR-kinase activity are required upstream in the FA/BRCA pathway. The ability of Trichostatin-A and Wortmannin to inhibit foci formation was confirmed in dose-response and time course studies (date not shown) subsequently. The activity of these agents in this in vitro assay suggests that these agents will chemosensitize tumors to radiation and chemotherapy in vivo.

Photomicrographs of individual cells from the screening assay are shown in FIG. 7. Initially, approximately 1000 known bioactive compounds were screened. An agent which reduces by at least 10%, for example 10%, 20%, 30%, 50%, 75%, or up to 100%, the number and size of foci formed upon exposure to genotoxic agents such as ionizing radiation (IR) is indicative of an agent which inhibits formation of FANCD2-containing foci. In another screen, an agent which, in the absence of exposure to genotoxic agent, causes an at least 10%, for example 10%, 20%, 30%, 50%, 75%, 100%, 200% or 500%, increase in formation of FANCD2-containing foci relative to unexposed control cells is indicative of an agent which activates formation of FANCD2-containing foci. The vast majority of these compounds had no effect on the ability of Clone 7 cells to form GFP-FANCD2 foci after exposure IR. At least three relevant compounds emerged from the initial screen, two functioning as inhibitors of the pathway, and one functioning as an activator of the pathway.

A) Inhibitors of the FA/BRCA Pathway.

One inhibitor of the FA/BRCA pathway was the compound wortmannin. Wortmannin is a known inhibitor of the DNA damage response kinases, ATM and ATR. ATR kinase has been shown to be an upstream component of the FA/BRCA pathway, functioning as part of the molecular sensor apparatus of the pathway (see FIG. 8, below).

More selective libraries of compounds, enriched with novel kinase inhibitors are screened to determine if any of these compounds act specifically as inhibitors of the FA/BRCA pathway.

Another inhibitor of the FA/BRCA pathway identified was Trichostatin-A. Trichostatin-A is a known inhibitor of a broad class of enzymes known as HDACs (Histone Deacetylases). There are at least eight different HDAC enzymes in human cells. Importantly, HDAC inhibitors, such as Trichostatin-A (Beppu et al., (1990) J Biol. Chem. 265, 17174-9) and SAHA (Richon et al., Proc Natl Acad Sci USA. (1998) 95, 3003-7), have potent anti-tumor activity in vitro and in vivo, and this class of drugs is currently under intense investigation as a new class of human anti-neoplastic agents.

The identification (and confirmation) of Trichostatin-A as an inhibitor of the FA/BRCA pathway has important implications. For instance:

1) Now, other HDAC inhibitors, some of which are in clinical trials in cancer patients, can be tested directly for their ability to inhibit the FA/BRCA pathway. In fact, FA/BRCA pathway in clone 7 cells may provide a useful biomarker for the effectiveness of new HDAC inhibitors.
2) While HDAC inhibitors have broad effects on cellular function (affecting DNA repair, transcription, and mitogenesis), in fact the disruption of the FA/BRCA pathway may be the relevant "readout" in assessing the potency of a given HDAC inhibitor derivative compound.
3) HDAC inhibitors may in fact function as radiosensitizers and chemosensitizers of cancer cells, by inhibiting DNA repair through the FA/BRCA pathway. Accordingly, HDAC inhibitors may be delivered most effectively in combination with radiation or cytotoxic DNA damaging drugs (i.e., cisplatin).

B) Agonists of the FA/BRCA Pathway.

Desferrioxamine (DFO) was identified as an agonist of the FA/BRCA pathway. DFO is a potent activator of FANCD2 monoubiquitination and foci assembly. DFO is a known chelator of iron, and it is believed to decrease intracellular oxygen radicals, but its role in activating the FANCD2 monoubiquitination and foci formation has not been previously demonstrated.

Example 5

Determination of the Molecular Sensor Apparatus of the FA/BRCA Pathway

Figure 8A:
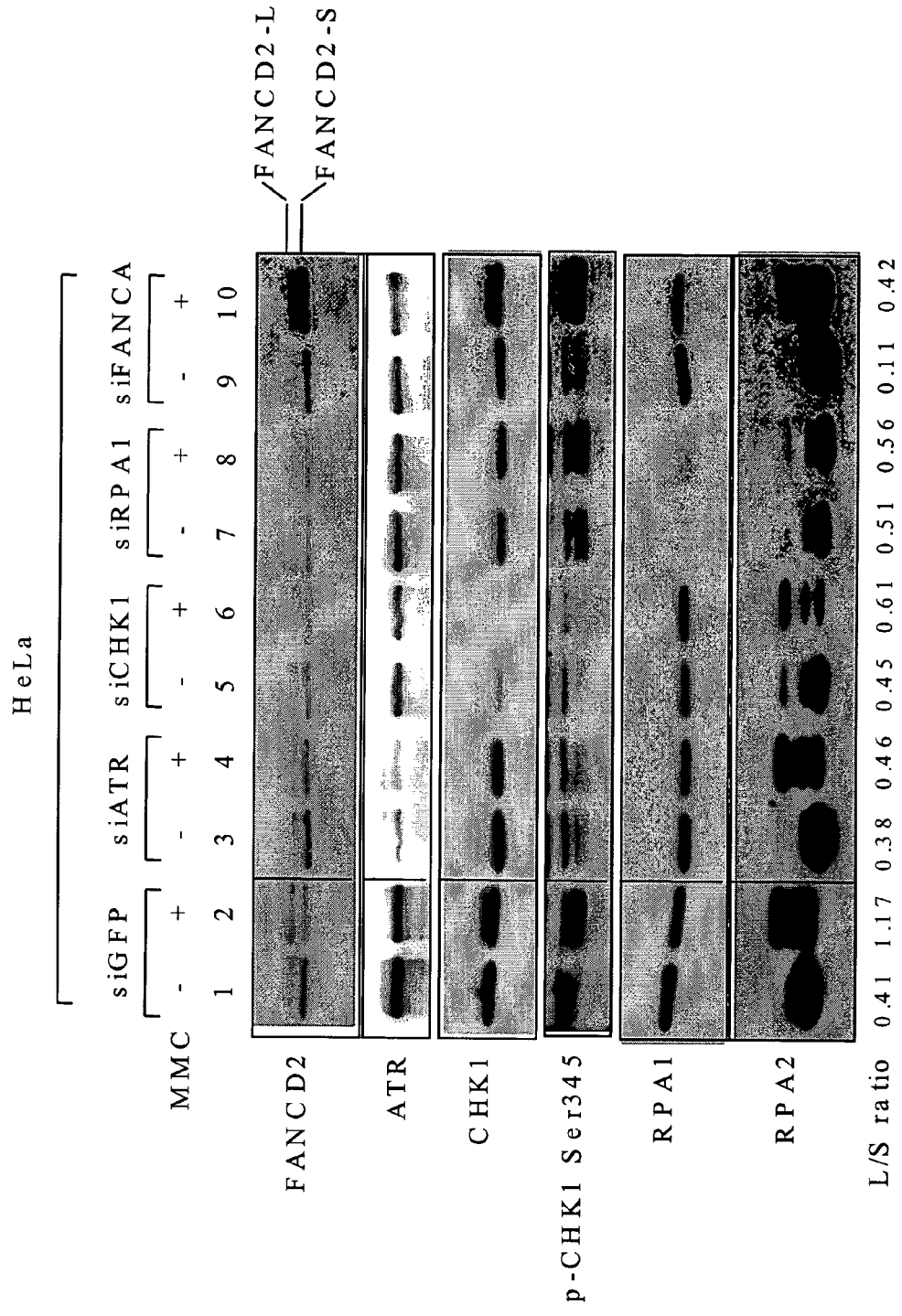
FIG. 8. The cellular signaling proteins ATR, RPA1, and CHK1 are required upstream in the FA/BRCA signaling pathway. The inhibition of GFP-FANCD2 foci assembly by wortmannin suggested that the RPA1/ATR/CHK1 pathway may function as a sensor upstream in this pathway. siRNA inhibition was used to block the RPA1/ATR/CHK1 pathway. Transient transfection with siRNAs for RPA1, ATR, or CHK1 resulted in loss of expression of the corresponding cellular proteins. Interestingly, there was a decrease in the MMC (A) and IR (B) inducible monoubiquitination of FANCD2 in these treated cells, as judged by the decrease in FANCD2-L/FANCD2-S ratio. Cells were transfected with siRNA specific for the FANCA gene (lanes 9, 10). siRNA to FANCA decreased FANCA expression (not shown) and decreased the FANCD2-L/FANCD2-S ratio, further demonstrating that FANCA works upstream in the FA pathway.
Figure 8B:
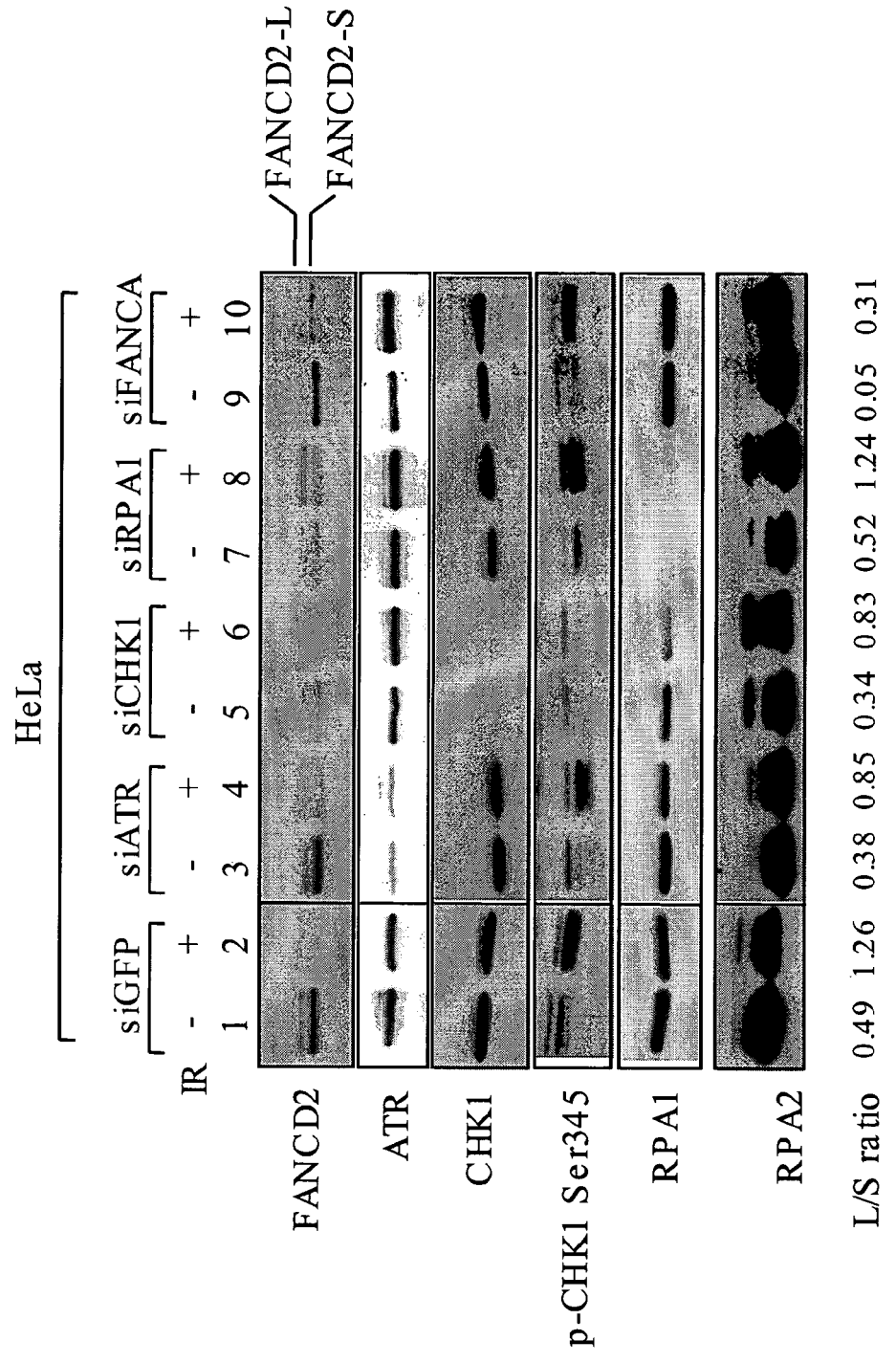

Wortmannin, a known inhibitor of ATM and ATR kinases, was shown to block FANCD2 monoubiquitination and foci formation. Accordingly, this result suggested to us that ATM (or ATR) may function upstream in the FA/BRCA pathway. To test this hypothesis, an siRNA strategy was used (FIG. 8, A, B). Inhibitory RNA molecules, specific for ATR, CHK1, and RPA1 (RPA1 is a known activator of ATR; CHK1 is a known substrate of ATR.) Interestingly, transient transfection of HeLa cells with these siRNA molecules (1) reduced MMC-inducible and IR-inducible monoubiquitination of FANCD2 (FIG. 8), (2) reduced FANCD2 foci formation (not shown) and sensitized the HeLa cells to MMC (not shown). An important feature of this assay (FIG. 8) is the calculation of the "L/S ratio." This ratio is calculated as the density of the FANCD2-L band divided by the density of the FANCD2-S band. These band intensities are determined directly from the autoradiograph. For instance (FIG. 8A), MMC activation results in an increase of the L/S ratio to 1.17; knockout of ATR, with siRNA, reduces the L/S ratio to 0.46 (unitless value).

Figure 9:
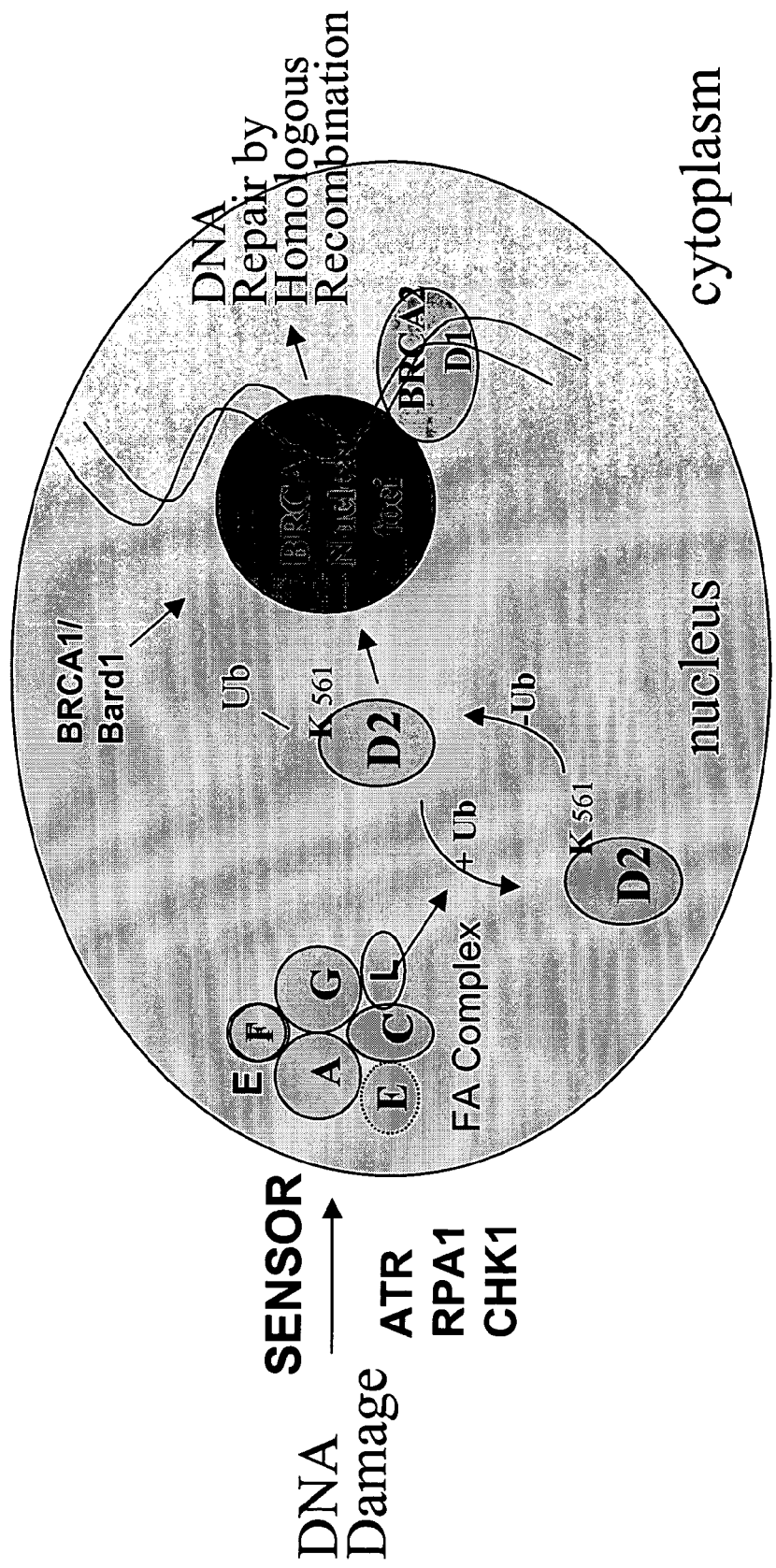
FIG. 9. Schematic model of the FA/BRCA pathway, showing upstream RPA1/ATR/CHK1 sensor apparatus. The general approach of siRNA inhibition is used to identify other upstream proteins in the FA/BRCA pathway. Inhibition of any of these upstream targets (say, inhibition of ATR, by Wortmannin) is a potential mechanism of knocking out the pathway and sensitizing human tumor cells to cisplatin or IR.

Based on these important observations, it is clear that the ATR/RPA1/CHK1 network of proteins works upstream in the FA/BRCA pathway (FIG. 9). Disruption of any of the steps upstream in this pathway, through pharmacological manipulation, can potentially radiosensitize or chemosensitize cancer cells to other conventional antineoplastic reagents.

Uses

The invention is useful in the detection of exposure of a living subject to genotoxic agents such as ionizing radiation. In addition, the invention is useful in determining the sensitivity of a living subject to genotoxic agents prior to exposure of such agents, for example for radiation therapy, and is useful in providing a more individualized therapy with reduced risk of overexposure of sensitive patients. The invention is also of use in identifying agents which alter the degree of foci formation. These agents could be useful as protective agents against DNA damage induced by genotoxic agents, or alternatively could be useful as chemosensitizing agents to be used in combination with chemotherapeutic drugs.

Other Embodiments

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

REFERENCES FOR THIS SECTION

DiTullio, R. A., Jr., Mochan, T. A., Venere, M., Bartkova, J., Sehested, M., Bartek, J., and Halazonetis, T. D. (2002). 53BP1 functions in an ATM-dependent checkpoint pathway that is constitutively activated in human cancer. Nat Cell Biol 4, 998-1002.

Garcia-Higuera, I., Taniguchi, T., Ganesan, S., Meyn, M. S., Timmers, C., Hejna, J., Grompe, M., and D'Andrea, A. D. (2001). Interaction of the Fanconi anemia proteins and BRCA1 in a common pathway. Mol Cell 7, 249-262.

Lou, Z., Chini, C. C., Minter-Dykhouse, K., and Chen, J. (2003). MDC1 regulates BRCA1 localization and phosphorylation in DNA damage checkpoint control. J Biol. Chem.

Paull, T. T., Rogakou, E. P., Yamazaki, V., Kirchgessner, C. U., Gellert, M., and Bonner, W. M. (2000). A critical role for histone H2AX in recruitment of repair factors to nuclear foci after DNA damage. Curr Biol 10, 886-895.

Scully, R., Chen, J., Ochs, R. L., Keegan, K., Hoekstra, M., Feunteun, J., and Livingston, D. M. (1997a). Dynamic changes of BRCA1 subnuclear location and phosphorylation state are initiated by DNA damage. Cell 90, 425-435.

Scully, R., Chen, J., Plug, A., Xiao, Y., Weaver, D., Feunteun, J., Ashley, T., and Livingston, D. M. (1997b). Association of BRCA1 with Rad51 in mitotic and meiotic cells. Cell 88, 265-275.

Scully, R., Puget, N., and Vlasakova, K. (2000). DNA polymerase stalling, sister chromatid recombination and the BRCA genes. Oncogene 19, 6176-6183.

Stewart, G. S., Wang, B., Bignell, C. R., Taylor, A. M., and Elledge, S. J. (2003). MDC1 is a mediator of the mammalian DNA damage checkpoint. Nature 421, 961-966.

Taniguchi, T., Garcia-Higuera, I., Xu, B., Andreassen, P. R., Gregory, R. C., Kim, S. T., Lane, W. S., Kastan, M. B., and D'Andrea, A. D. (2002). Convergence of the Fanconi anemia and ataxia telangiectasia signaling pathways. Cell 109, 459-472.

Wu, X., Petrini, J. H., Heine, W. F., Weaver, D. T., Livingston, D. M., and Chen, J. (2000). Independence of R/M/N focus formation and the presence of intact BRCA1. Science 289, 11.

What is claimed is:

1. A method of screening test agents which modulate formation of FANCD2-containing foci, said method comprising:
   - identifying an individual suspected of having been exposed to a genotoxic agent;
   - obtaining a biological sample from said individual;
   - contacting said biological sample with test compound; and
   - detecting the presence of FANCD2 in FANCD2-containing foci relative to a control sample, wherein a difference in the degree of foci formation relative to a control sample is indicative of an agent active in foci formation, wherein said biological sample is a cell expressing a polynucleotide comprising a DNA sequence encoding the human FACD2 protein of SEQ ID NO:1 fused in frame with a DNA sequence encoding a fluorescent protein.

2. The method of claim 1, wherein said detecting comprises fluorescence microscopy.

3. The method of claim 1, wherein said detecting comprises measuring fluorescence resonance energy transfer.

4. A method of screening test agents which modulate formation of FANCD2-containing foci, said method comprising:
   - identifying an individual suspected of having been exposed to a genotoxic agent;
   - obtaining a biological sample from said individual;
   - contacting said biological sample with test compound; and
   - detecting the presence of FANCD2 in FANCD2-containing foci relative to a control sample, wherein a difference in the degree of foci formation relative to a control sample is indicative of an agent active in foci formation, wherein said biological sample is a cell expressing a polynucleotide comprising a DNA sequence encoding a protein that binds with FANCD2 upon foci formation, fused in frame with a DNA sequence encoding a second fluorophore.

5. A method of screening test agents which modulate formation of FANCD2-containing foci, said method comprising:
   - identifying an individual suspected of having been exposed to a genotoxic agent;
   - obtaining a biological sample from said individual;
   - contacting said biological sample with test compound; and
   - detecting the presence of FANCD2 in FANCD2-containing foci relative to a control sample, wherein a difference in the degree of foci formation relative to a control sample is indicative of an agent active in foci formation, wherein said biological sample is a cell expressing a polynucleotide comprising a DNA sequence encoding the human FACD2 protein of SEQ ID NO:1 fused in frame with a DNA sequence encoding a fluorescent protein and a polynucleotide comprising a DNA sequence encoding a protein that binds with FANCD2 upon foci formation, fused in frame with a DNA sequence encoding a second fluorophore.

* * * * *

SEQUENCE LISTING

<160> NUMBER OF SEQ ID NOS: 3

<210> SEQ ID NO 1
<211> LENGTH: 1451
<212> TYPE: PRT
<213> ORGANISM: Homo sapiens

<400> SEQUENCE: 1

```
Met Val Ser Lys Arg Arg Leu Ser Lys Ser Glu Asp Lys Glu Ser Leu
1               5                   10                  15

Thr Glu Asp Ala Ser Lys Thr Arg Lys Gln Pro Leu Ser Lys Lys Thr
            20                  25                  30

Lys Lys Ser His Ile Ala Asn Ala Val Glu Glu Asn Asp Ser Ile Phe
        35                  40                  45

Val Lys Leu Leu Lys Ile Ser Gly Ile Ile Leu Lys Thr Gly Glu Ser
    50                  55                  60

Gln Asn Gln Leu Ala Val Asp Gln Ile Ala Phe Gln Lys Lys Leu Phe
65                  70                  75                  80

Gln Thr Leu Arg Arg His Pro Ser Tyr Pro Lys Ile Ile Glu Glu Phe
                85                  90                  95

Val Ser Gly Leu Glu Ser Tyr Ile Glu Asp Glu Asp Ser Phe Arg Asn
            100                 105                 110

Cys Leu Leu Ser Cys Glu Arg Leu Gln Asp Glu Glu Ala Ser Met Gly
        115                 120                 125

Ala Ser Tyr Ser Lys Ser Leu Ile Lys Leu Leu Leu Gly Ile Asp Ile
    130                 135                 140
```

-continued

```
Leu Gln Pro Ala Ile Ile Lys Thr Leu Phe Glu Lys Leu Pro Glu Tyr
145                 150                 155                 160

Phe Phe Glu Asn Arg Asn Ser Asp Glu Ile Asn Ile Phe Arg Leu Ile
                165                 170                 175

Val Ser Gln Leu Lys Trp Leu Asp Arg Val Val Asp Gly Lys Asp Leu
            180                 185                 190

Thr Thr Lys Ile Met Gln Leu Ile Ser Ile Ala Pro Glu Asn Leu Gln
        195                 200                 205

His Asp Ile Ile Thr Ser Lys Pro Glu Ile Leu Gly Asp Ser Gln His
    210                 215                 220

Ala Asp Val Gly Lys Glu Leu Ser Asp Leu Leu Ile Glu Asn Thr Ser
225                 230                 235                 240

Leu Thr Val Pro Ile Leu Asp Val Leu Ser Ser Leu Arg Leu Asp Pro
                245                 250                 255

Asn Phe Leu Leu Lys Val Arg Gln Leu Val Met Asp Lys Leu Ser Ser
                260                 265                 270

Ile Arg Leu Glu Asp Leu Pro Val Ile Ile Lys Phe Ile Leu His Ser
            275                 280                 285

Val Thr Ala Met Asp Thr Leu Glu Val Ile Ser Glu Leu Arg Glu Lys
        290                 295                 300

Leu Asp Leu Gln His Cys Val Leu Pro Ser Arg Leu Gln Ala Ser Gln
305                 310                 315                 320

Val Lys Leu Lys Ser Lys Gly Arg Ala Ser Ser Gly Asn Gln Glu
                325                 330                 335

Ser Ser Gly Gln Ser Cys Ile Ile Leu Leu Phe Asp Val Ile Lys Ser
            340                 345                 350

Ala Ile Arg Tyr Glu Lys Thr Ile Ser Glu Ala Trp Ile Lys Ala Ile
        355                 360                 365

Glu Asn Thr Ala Ser Val Ser Glu His Lys Val Phe Asp Leu Val Met
    370                 375                 380

Leu Phe Ile Ile Val Ser Thr Asn Thr Gln Thr Lys Lys Tyr Ile Asp
385                 390                 395                 400

Arg Val Leu Arg Asn Lys Ile Arg Ser Gly Cys Ile Gln Glu Gln Leu
                405                 410                 415

Leu Gln Ser Thr Phe Ser Val His Tyr Leu Val Leu Lys Asp Met Cys
            420                 425                 430

Ser Ser Ile Leu Ser Leu Ala Gln Ser Leu Leu His Ser Leu Asp Gln
        435                 440                 445

Ser Ile Ile Ser Phe Gly Ser Leu Leu Tyr Lys Tyr Ala Phe Lys Phe
    450                 455                 460

Phe Asp Thr Tyr Cys Gln Gln Glu Val Val Gly Ala Leu Val Thr His
465                 470                 475                 480

Ile Cys Ser Gly Asn Glu Ala Glu Val Asp Asp Ala Leu Asp Val Leu
                485                 490                 495

Leu Glu Leu Val Val Leu Asn Pro Ser Ala Met Met Met Asn Ala Val
            500                 505                 510

Phe Val Gln Gly Ile Leu Asp Tyr Leu Asp Asn Ile Ser Pro Gln Gln
        515                 520                 525

Ile Arg Lys Leu Phe Tyr Val Leu Ser Thr Leu Ala Phe Ser Lys Gln
    530                 535                 540

Asn Glu Ala Ser Ser His Ile Gln Asp Asp Met His Leu Val Ile Arg
545                 550                 555                 560

Lys Gln Leu Ser Ser Thr Val Phe Lys Tyr Lys Leu Ile Gly Ile Ile
```

-continued

```
                565                 570                 575
Gly Ala Val Thr Met Ala Gly Ile Met Ala Ala Asp Arg Ser Glu Ser
                580                 585                 590
Pro Ser Leu Thr Gln Glu Arg Ala Asn Leu Ser Asp Glu Gln Cys Thr
                595                 600                 605
Gln Val Thr Ser Leu Leu Gln Leu Val His Ser Cys Ser Glu Gln Ser
                610                 615                 620
Pro Gln Ala Ser Ala Leu Tyr Tyr Asp Glu Phe Ala Asn Leu Ile Gln
625                 630                 635                 640
His Glu Lys Leu Asp Pro Lys Ala Leu Glu Trp Val Gly His Thr Ile
                645                 650                 655
Cys Asn Asp Phe Gln Asp Ala Phe Val Val Asp Ser Cys Val Val Pro
                660                 665                 670
Glu Gly Asp Phe Pro Phe Pro Val Lys Ala Leu Tyr Gly Leu Glu Glu
                675                 680                 685
Tyr Asp Thr Gln Asp Gly Ile Ala Ile Asn Leu Pro Leu Leu Phe
                690                 695                 700
Ser Gln Asp Phe Ala Lys Asp Gly Gly Pro Val Thr Ser Gln Glu Ser
705                 710                 715                 720
Gly Gly Lys Leu Val Ser Pro Leu Cys Leu Ala Pro Tyr Phe Arg Leu
                725                 730                 735
Leu Arg Leu Cys Val Glu Arg Gln His Asn Gly Asn Leu Glu Glu Ile
                740                 745                 750
Asp Gly Leu Leu Asp Cys Pro Ile Phe Leu Thr Asp Leu Glu Pro Gly
                755                 760                 765
Glu Lys Leu Glu Ser Met Ser Ala Lys Glu Ala Ser Phe Met Cys Ser
770                 775                 780
Leu Ile Phe Leu Thr Leu Asn Trp Phe Arg Glu Ile Val Asn Ala Phe
785                 790                 795                 800
Cys Gln Glu Thr Ser Pro Glu Asn Lys Gly Lys Val Leu Thr Arg Leu
                805                 810                 815
Lys His Ile Val Glu Leu Gln Ile Leu Leu Glu Lys Tyr Leu Ala Val
                820                 825                 830
Thr Pro Asp Tyr Val Pro Pro Leu Gly Asn Phe Asp Val Glu Thr Leu
                835                 840                 845
Asp Ile Thr Pro His Thr Val Thr Ala Ile Ser Ala Lys Ile Arg Lys
                850                 855                 860
Lys Gly Lys Ile Glu Arg Lys Gln Lys Thr Asp Gly Ser Lys Thr Ser
865                 870                 875                 880
Ser Ser Asp Thr Leu Ser Glu Glu Lys Asn Ser Glu Cys Asp Pro Thr
                885                 890                 895
Pro Ser His Arg Gly Gln Leu Asn Lys Glu Phe Thr Gly Lys Glu Glu
                900                 905                 910
Lys Thr Ser Leu Leu His Asn Ser His Ala Phe Phe Arg Glu Leu
                915                 920                 925
Asp Ile Glu Val Phe Ser Ile Leu His Cys Gly Leu Val Thr Lys Phe
                930                 935                 940
Ile Leu Asp Thr Glu Met His Thr Glu Ala Thr Glu Val Val Gln Leu
945                 950                 955                 960
Gly Pro Pro Glu Leu Leu Phe Leu Leu Glu Asp Leu Ser Gln Lys Leu
                965                 970                 975
Glu Ser Met Leu Thr Pro Pro Ile Ala Arg Arg Val Pro Phe Leu Lys
                980                 985                 990
```

-continued

```
Asn Lys Gly Ser Arg Asn Ile Gly  Phe Ser His Leu Gln  Gln Arg Ser
        995              1000                1005

Ala Gln  Glu Ile Val His Cys  Val Glu Gln Leu Leu  Thr Pro Met
    1010             1015               1020

Cys Asn  His Leu Glu Asn Ile  His Asn Tyr Ile Gln  Cys Leu Ala
    1025             1030               1035

Ala Glu  Asn His Gly Val Val  Asp Gly Pro Gly Val  Lys Val Gln
    1040             1045               1050

Glu Tyr  His Ile Met Ser Ser  Cys Tyr Gln Arg Leu  Leu Gln Ile
    1055             1060               1065

Phe His  Gly Leu Phe Ala Trp  Ser Gly Phe Ser Gln  Pro Glu Asn
    1070             1075               1080

Gln Asn  Leu Leu Tyr Ser Ala  Leu His Val Leu Ser  Ser Arg Leu
    1085             1090               1095

Lys Gln  Gly Glu His Ser Gln  Pro Leu Glu Glu Leu  Leu Ser Gln
    1100             1105               1110

Ser Val  His Tyr Leu Gln Asn  Phe His Gln Ser Ile  Pro Ser Phe
    1115             1120               1125

Gln Cys  Ala Leu Tyr Leu Ile  Arg Leu Leu Met Val  Ile Leu Glu
    1130             1135               1140

Lys Ser  Thr Ala Ser Ala Gln  Asn Lys Glu Lys Ile  Ala Ser Leu
    1145             1150               1155

Ala Arg  Gln Phe Leu Cys Arg  Val Trp Pro Ser Gly  Asp Lys Glu
    1160             1165               1170

Lys Ser  Asn Ile Ser Asn Asp  Gln Leu His Ala Leu  Leu Cys Ile
    1175             1180               1185

Tyr Leu  Glu His Thr Glu Ser  Ile Leu Lys Ala Ile  Glu Glu Ile
    1190             1195               1200

Ala Gln  Val Gly Val Pro Glu  Leu Ile Asn Ser Pro  Lys Asp Ala
    1205             1210               1215

Ser Ser  Ser Thr Phe Pro Thr  Leu Thr Arg His Thr  Pro Val Val
    1220             1225               1230

Phe Phe  Arg Val Met Met Ala  Glu Leu Glu Lys Ile  Val Lys Lys
    1235             1240               1245

Ile Glu  Pro Gly Thr Ala Ala  Asp Ser Gln Gln Ile  His Glu Glu
    1250             1255               1260

Lys Leu  Leu Tyr Trp Asn Met  Ala Val Arg Asp Phe  Ser Ile Leu
    1265             1270               1275

Ile Asn  Leu Ile Lys Val Phe  Asp Ser His Pro Val  Leu His Val
    1280             1285               1290

Cys Leu  Lys Val Gly Arg Leu  Phe Val Glu Ala Phe  Leu Lys Gln
    1295             1300               1305

Cys Met  Pro Leu Leu Asp Ile  Ser Phe Arg Lys His  Arg Glu Asp
    1310             1315               1320

Val Leu  Ser Leu Leu Glu Thr  Phe Gln Leu Asp Thr  Arg Leu Leu
    1325             1330               1335

His His  Leu Cys Gly His Ser  Lys Ile His Gln Asp  Thr Arg Leu
    1340             1345               1350

Thr Gln  His Val Pro Leu Leu  Lys Lys Thr Leu Glu  Leu Leu Val
    1355             1360               1365

Cys Arg  Val Lys Ala Met Leu  Thr Leu Asn Asn Cys  Arg Glu Ala
    1370             1375               1380
```

-continued

```
Phe Trp Leu Gly Asn Leu Lys Asn Arg Asp Leu Gln Gly Glu Glu
    1385                1390                1395

Ile Lys Ser Gln Asn Ser Gln Glu Ser Thr Ala Asp Glu Ser Glu
    1400                1405                1410

Asp Asp Met Ser Ser Gln Ala Ser Lys Ser Lys Ala Thr Glu Asp
    1415                1420                1425

Gly Glu Glu Asp Glu Val Ser Ala Gly Glu Lys Glu Gln Asp Ser
    1430                1435                1440

Asp Glu Ser Tyr Asp Asp Ser Asp
    1445                1450

<210> SEQ ID NO 2
<211> LENGTH: 13
<212> TYPE: PRT
<213> ORGANISM: Homo sapiens

<400> SEQUENCE: 2

Asp Met His Leu Val Ile Arg Lys Gln Leu Ser Ser Thr
1               5                   10

<210> SEQ ID NO 3
<211> LENGTH: 7
<212> TYPE: PRT
<213> ORGANISM: Artificial
<220> FEATURE:
<223> OTHER INFORMATION: Peptide Sequence corresponding to the
      C-terminus of Ubiquitin

<400> SEQUENCE: 3

Gly Gly Arg Leu Arg Leu Cys
1               5
```